(12) United States Patent
Oral et al.

(10) Patent No.: US 12,115,289 B2
(45) Date of Patent: Oct. 15, 2024

(54) DRUG ELUTING POLYMER COMPOSED OF BIODEGRADABLE POLYMERS APPLIED TO SURFACE OF MEDICAL DEVICE

(71) Applicant: THE GENERAL HOSPITAL CORPORATION, Boston, MA (US)

(72) Inventors: Ebru Oral, Newton, MA (US); Jeremy V. Suhardi, Boston, MA (US); Orhun K. Muratoglu, Cambridge, MA (US); Henrik Malchau, Cambridge, MA (US); Harry E. Rubash, Marco Island, FL (US); Andrew A. Freiberg, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 741 days.

(21) Appl. No.: 16/074,256

(22) PCT Filed: Feb. 3, 2017

(86) PCT No.: PCT/US2017/016506
§ 371 (c)(1),
(2) Date: Jul. 31, 2018

(87) PCT Pub. No.: WO2017/136726
PCT Pub. Date: Aug. 10, 2017

(65) Prior Publication Data
US 2021/0178027 A1 Jun. 17, 2021

Related U.S. Application Data

(60) Provisional application No. 62/291,856, filed on Feb. 5, 2016.

(51) Int. Cl.
| | |
|---|---|
| *A61L 31/16* | (2006.01) |
| *A61K 45/06* | (2006.01) |
| *A61L 27/34* | (2006.01) |
| *A61L 27/54* | (2006.01) |
| *A61L 27/58* | (2006.01) |
| *A61L 29/08* | (2006.01) |
| *A61L 29/14* | (2006.01) |
| *A61L 29/16* | (2006.01) |
| *A61L 31/10* | (2006.01) |
| *A61L 31/14* | (2006.01) |
| *C08F 2/44* | (2006.01) |
| *C08L 71/02* | (2006.01) |
| *A61K 31/496* | (2006.01) |
| *A61K 31/7052* | (2006.01) |

(52) U.S. Cl.
CPC ............. *A61L 31/16* (2013.01); *A61K 45/06* (2013.01); *A61L 27/34* (2013.01); *A61L 27/54* (2013.01); *A61L 27/58* (2013.01); *A61L 29/085* (2013.01); *A61L 29/148* (2013.01); *A61L 29/16* (2013.01); *A61L 31/10* (2013.01); *A61L 31/148* (2013.01); *C08F 2/44* (2013.01); *C08L 71/02* (2013.01); *A61K 31/496* (2013.01); *A61K 31/7052* (2013.01); *A61L 2300/418* (2013.01); *A61L 2400/04* (2013.01)

(58) Field of Classification Search
CPC .......... C08L 71/02; A61L 29/16; A61L 31/16; A61L 27/34; A61L 27/58; A61L 29/085; A61L 29/148; A61L 31/10; A61L 31/148; A61L 27/54; A61L 2300/418; A61L 2400/04; C08F 299/024; C08F 2/44; A61K 31/7052; A61K 31/705; A61K 45/06; A61K 31/496; C08G 63/08
See application file for complete search history.

(56) References Cited

U.S. PATENT DOCUMENTS

| | | | |
|---|---|---|---|
| 4,663,358 A | 5/1987 | Hyon et al. | |
| 4,750,482 A | 6/1988 | Sieverding | |
| 4,920,158 A | 4/1990 | Murray et al. | |
| 5,410,016 A * | 4/1995 | Hubbell | A61K 9/1635 |
| | | | 128/898 |
| 5,522,898 A | 6/1996 | Bao | |
| 5,540,033 A | 7/1996 | Fox et al. | |

(Continued)

FOREIGN PATENT DOCUMENTS

| | | |
|---|---|---|
| EP | 0881919 A1 | 12/1998 |
| EP | 1223182 | 7/2002 |

(Continued)

OTHER PUBLICATIONS

Aleyamma et al. "Polyvinyl Alcohol as a Biomaterial" 1991, Blood Compatible Materials and Devices: Perspective Towards the 21st Century, p. 123.
Bourne "Prophylactic Use of Antibiotic Bone Cement an Emerging Standard—in the Affirmative" 2004, J. of Arthroplasty 19(4)(Supp 1):69-72.

(Continued)

*Primary Examiner* — Anna R Falkowitz
(74) *Attorney, Agent, or Firm* — McCarter & English, LLP; John P. Isacson

(57) ABSTRACT

This present invention relates to drug eluting polymers, including novel biodegradable drug eluting polymers, which are added to the surface of a medical device to treat device associated complications and to deliver drug locally around the device. Methods of making polymers, for example, drug-eluting polymers, polymer compositions, and materials used therewith also are provided. The drug eluting polymers are obtained from the polymerization of macromonomers made of a connecting moiety, a biodegradable moiety and a cross-linkable moiety that are liquids at a temperature of 10° C. to 40° C.

18 Claims, 21 Drawing Sheets

(56) References Cited

U.S. PATENT DOCUMENTS

| | | |
|---|---|---|
| 5,705,780 A | 1/1998 | Bao |
| 5,827,904 A | 10/1998 | Hahn |
| 5,846,214 A | 12/1998 | Makuuchi et al. |
| 5,879,400 A | 3/1999 | Merrill et al. |
| 5,981,826 A | 11/1999 | Ku et al. |
| 6,165,220 A | 12/2000 | McKellop et al. |
| 6,365,089 B1 | 4/2002 | Krebs et al. |
| 6,448,315 B1 | 9/2002 | Lidgren et al. |
| 6,641,617 B1 | 11/2003 | Merrill et al. |
| 6,818,171 B2 | 11/2004 | Wang et al. |
| 6,852,772 B2 | 2/2005 | Muratoglu et al. |
| 6,855,165 B2 | 2/2005 | Fell et al. |
| 6,855,743 B1 | 2/2005 | Gvozdic |
| 6,866,684 B2 | 3/2005 | Fell et al. |
| 6,911,044 B2 | 6/2005 | Fell et al. |
| 6,923,831 B2 | 8/2005 | Fell et al. |
| 6,951,654 B2 | 10/2005 | Malcolm et al. |
| 6,960,617 B2 | 11/2005 | Omidian et al. |
| 7,205,339 B2 | 4/2007 | Muratoglu |
| 7,282,165 B2 | 10/2007 | Williams, III et al. |
| 7,380,752 B2 | 6/2008 | Guard et al. |
| 7,381,752 B2 | 6/2008 | Muratoglu |
| 7,431,874 B2 | 10/2008 | Muratoglu et al. |
| 7,858,671 B2 | 12/2010 | Merrill et al. |
| 8,133,501 B2 | 3/2012 | Li et al. |
| 8,420,000 B2 | 4/2013 | Muratoglu et al. |
| 8,425,815 B2 | 4/2013 | Muratoglu et al. |
| 8,461,225 B2 | 6/2013 | Muratoglu et al. |
| 8,530,057 B2 | 9/2013 | Muratoglu et al. |
| 8,569,395 B2 | 10/2013 | Muratoglu et al. |
| 8,920,491 B2 * | 12/2014 | Flanagan ............... A61L 31/16 623/1.44 |
| 8,933,145 B2 | 1/2015 | Oral et al. |
| 9,168,683 B2 | 10/2015 | Muratoglu et al. |
| 9,220,811 B2 | 12/2015 | Overstreet et al. |
| 9,273,189 B2 | 3/2016 | Muratoglu et al. |
| 9,370,878 B2 | 6/2016 | Muratoglu et al. |
| 9,394,384 B2 | 7/2016 | Muratoglu et al. |
| 9,433,705 B2 | 9/2016 | Muratoglu et al. |
| 9,445,901 B2 | 9/2016 | Tunc et al. |
| 9,937,278 B2 | 4/2018 | Steinberg et al. |
| 11,850,329 B2 | 12/2023 | Oral et al. |
| 2001/0003796 A1 * | 6/2001 | Yang ............... C08L 71/02 604/265 |
| 2002/0107330 A1 | 8/2002 | Pinchuk et al. |
| 2002/0132961 A1 * | 9/2002 | Siol ............... A61K 6/887 528/272 |
| 2003/0044585 A1 | 3/2003 | Taylor et al. |
| 2003/0232895 A1 | 12/2003 | Omidian et al. |
| 2004/0092653 A1 | 5/2004 | Ruberti et al. |
| 2004/0133275 A1 | 7/2004 | Mansmann |
| 2004/0171740 A1 | 9/2004 | Ruberti et al. |
| 2004/0180072 A1 | 9/2004 | Tunc et al. |
| 2004/0220296 A1 | 11/2004 | Lowman et al. |
| 2005/0048121 A1 | 3/2005 | East et al. |
| 2005/0049323 A1 | 3/2005 | Gvozdic |
| 2005/0148682 A1 | 7/2005 | Hu et al. |
| 2005/0287187 A1 | 12/2005 | Mansmann |
| 2006/0079597 A1 | 4/2006 | Muratoglu et al. |
| 2006/0083773 A1 | 4/2006 | Myung et al. |
| 2007/0077268 A1 | 4/2007 | King et al. |
| 2007/0100015 A1 | 5/2007 | Hubbell et al. |
| 2007/0141106 A1 | 6/2007 | Bonutti et al. |
| 2007/0191504 A1 | 8/2007 | Muratoglu |
| 2007/0213835 A1 | 9/2007 | Wimmer et al. |
| 2009/0118390 A1 | 5/2009 | Abt et al. |
| 2009/0263319 A1 | 10/2009 | Wohabrebbi et al. |
| 2011/0136935 A1 * | 6/2011 | Khor ............... A61K 6/54 523/116 |
| 2012/0041094 A1 | 2/2012 | Oral et al. |
| 2012/0052292 A1 | 3/2012 | Pulapura et al. |
| 2014/0024736 A1 | 1/2014 | Thomas et al. |
| 2014/0175693 A1 | 6/2014 | Liu |
| 2015/0151866 A1 | 6/2015 | Oral et al. |
| 2015/0290280 A1 | 10/2015 | Petrak et al. |
| 2016/0215117 A1 | 7/2016 | Muratoglu et al. |
| 2016/0250779 A1 | 9/2016 | Muratoglu et al. |
| 2018/0318468 A1 | 11/2018 | Oral et al. |
| 2019/0160207 A1 | 5/2019 | Suhardi et al. |
| 2021/0228775 A1 | 7/2021 | Oral et al. |
| 2022/0143053 A1 | 5/2022 | Muratoglu et al. |
| 2023/0190655 A1 | 6/2023 | Muratoglu et al. |
| 2023/0256139 A1 | 8/2023 | Suhardi et al. |

FOREIGN PATENT DOCUMENTS

| | | | |
|---|---|---|---|
| EP | 1223182 A1 | 7/2002 | |
| EP | 1457172 A1 | 9/2004 | |
| EP | 1779877 A1 | 5/2007 | |
| EP | 2907834 | 8/2015 | |
| EP | 2907834 A2 | 8/2015 | |
| JP | 1-270867 A | 10/1989 | |
| JP | H01-270867 A | 10/1989 | |
| JP | 5-504689 A | 7/1993 | |
| JP | H05-504689 A | 7/1993 | |
| JP | 5-230313 A | 9/1993 | |
| JP | H05-230313 A | 9/1993 | |
| JP | 2000-204165 A | 7/2000 | |
| JP | 2008-49129 A | 3/2008 | |
| WO | 1997029793 A | 8/1997 | |
| WO | 1999/029793 A1 | 6/1999 | |
| WO | 1999/052474 A1 | 10/1999 | |
| WO | 1999052474 A | 10/1999 | |
| WO | 2001/005337 A1 | 1/2001 | |
| WO | 2001/080778 A1 | 11/2001 | |
| WO | 2002/048259 A2 | 6/2002 | |
| WO | 2004/032987 A1 | 4/2004 | |
| WO | 2006125082 A2 | 11/2006 | |
| WO | 2006/132661 A1 | 12/2006 | |
| WO | 2007/024684 A2 | 3/2007 | |
| WO | 2007/056667 A2 | 5/2007 | |
| WO | 2006/125082 A3 | 9/2007 | |
| WO | 2007/139744 A2 | 12/2007 | |
| WO | 2008/092047 A1 | 7/2008 | |
| WO | 2008/109098 A2 | 9/2008 | |
| WO | 2008/131410 A1 | 10/2008 | |
| WO | 2008/131451 A2 | 10/2008 | |
| WO | 2008131451 A1 | 10/2008 | |
| WO | 2009/032921 A1 | 3/2009 | |
| WO | 2010/096771 A2 | 8/2010 | |
| WO | 2011/029867 A1 | 3/2011 | |
| WO | WO 2011/029867 | 3/2011 | |
| WO | 2012/061499 A1 | 5/2012 | |
| WO | 2013/151950 A1 | 10/2013 | |
| WO | 2013/170005 A1 | 11/2013 | |
| WO | 2014/098603 A1 | 6/2014 | |
| WO | WO 2014/098603 * | 6/2014 | ............ A61L 27/28 |
| WO | 2017/083476 A1 | 5/2017 | |
| WO | 2017/136726 A1 | 8/2017 | |
| WO | 2017/192347 A1 | 11/2017 | |
| WO | 2020/102186 A1 | 5/2020 | |

OTHER PUBLICATIONS

Bragdon et al. "A New Pin-on-disk Wear Testing Method for Simulating Wear of Polyethylene on Cobalt-chrome Alloy in Total Hip Arthroplasty" 2001, The Journal of Arthroplasty 16(5):658-665.

Espehaug et al. "Antibiotic Prophylaxis in Total Hip Arthroplasty: Review of 10,905 Primary Cemented Total Hip Replacements Reported to the Norwegian Arthroplasty Register, 1987-1995" 1997, J. Bone Joint. Surg. Br. 790:590.

European Extended Search Report for EP 07784150 mailed Jan. 13, 2010.

European Supplementary Search Report for EP 08829042 mailed Dec. 23, 2010.

Gogja et al. "Local Antibiotic Therapy in Osteomyelitis" 2009, Semin. Plast. Surg. 23(2):100-107.

Gong et al. "Double-Network Hydrogels with Extremely High Mechanical Strength" Jul. 2003, Adv. Mater. 15(14):1155-1158.

Gristina "Implant Failure and the Immune-Incompetent Fibro-Inflammatory Zone" Jan. 1994, Clin. Orthop. Relat. Res. 298:106-118.

(56) References Cited

OTHER PUBLICATIONS

International Search Report and Written Opinion for PCT/US2001/047507 dated Jul. 30, 2002.
International Search Report and Written Opinion for PCT/US2005/034662 dated Jan. 25, 2006.
International Search Report and Written Opinion for PCT/US2008/061250 dated Jul. 18, 2008.
International Search Report and Written Opinion for PCT/US2008/061388 dated Sep. 25, 2008.
International Search Report and Written Opinion for PCT/US2008/075252 dated Dec. 3, 2008.
International Search Report and Written Opinion for PCT/US2017/016506 dated Jul. 17, 2017.
Jahan et al. "Combined Chemical and Mechanical Effects on Free Radicals in UHMWPE Joints During Implantation" 1991, J. Biomed. Mater. Res. 25(8):1005-1017.
Kashiwabara et al. "Free Radicals and Crosslinking in Irradiated Polyethylene" 1991, Radiation Physics and Chemistry 37(1):43-46.
Kobayashi et al. "Preliminary Study of Polyvinyl Alcohol-Hydrogel (PVA-H) Artificial Meniscus" 2003, Biomaterials 24(4):639-647.
Response to European Extended Search Report for EP 08829042 dated Jul. 21, 2011.
Spellburg et al. "Systemic Antibiotic Therapy for Chronic Osteomyelitis in Adults" 2012 Clin. Infect. Dis. 54(3):393-407.
Sutula et al. "The Otto Aufranc Award: Impact of Gamma Sterilization on Clinical Performance of Polyethylene in the Hip" 1995, Clinical Orthopaedics & Related Reserach 319:28-40.
Tanaka et al. "Novel Hydrogels with Excellent Mechanical Performance" 2005, Prog. Polym. Sci. 30(1):1-9.
Thomas et al. "The Effect of Dehydration History on PVA/PVP Hydrogels for Nucleus Pulposus Replacement" May 15, 2004, J. Biomed. Mater. Res. 69(2):135-140.
Van de Belt et al. "Surface Roughness, Porosity and Wettability of Gentamicin-loaded Bone Cements and Their Antibiotic Release" 2000, Biomaterials 21:1981-1987.
U.S. Appl. No. 16/098,233, filed Nov. 1, 2018, 2019-0160207, Abandoned.
U.S. Appl. No. 18/138,588, filed Apr. 24, 2023, 2023-0566139, Published.
U.S. Appl. No. 17/291,588, filed May 5, 2021, 2023-0190655, Published.
U.S. Appl. No. 17/437,912, filed Sep. 10, 2021, 2022-0143053, Published.
Ajandouz et al., Effects of pH on Caramelization and Maillard Reaction Kinetics in Fructose-Lysine Model Systems. Journal of Food Science. 2001;66(7):926-931.
Aleyamma et al., Polyvinyl Alcohol as a Biomaterial. Blood Compatible Materials and Devices, Perspectives Towards the 21st Century. Chandra P. Sharma (Ed). Technomic Publishing Co., Inc., Lancaster. Chapter 6, pp. 123-130, (1991).
Bourne, Prophylactic use of antibiotic bone cement: an emerging standard—in the affirmative. J Arthroplasty. Jun. 2004; 19(4 Suppl 1):69-72.
Bragdon et al., A new pin-on-disk wear testing method for simulating wear of polyethylene on cobalt-chrome alloy in total hip arthroplasty. J Arthroplasty. Aug. 2001;16(5):658-65.
Darouiche, Device-associated infections: a macroproblem that starts with microadherence. Clin Infect Dis. Nov. 1, 2001;33(9):1567-72.
De Kok et al., Reactivity of Peptides in the Maillard Reaction. Thermally Generated Flavors, Maillard, Microwave, and Extrusion Processes. American Chemical Society. Chapter 13, pp. 158-179, Nov. 30, 1993.
Eichner et al., Detection of Amadori Compounds in Heated Foods. Thermally Generated Flavors, Maillard, Microwave, and Extrusion Processes. American Chemical Society. Chapter 15, pp. 42-54, Nov. 30, 1993.

Esperhaug et al., Antibiotic prophylaxis in total hip arthroplasty. Review of 10,905 primary cemented total hip replacements reported to the Norwegian arthroplasty register, 1987 to 1995. J Bone Joint Surg Br. Jul. 1997;79(4):590-5.
Gogia et al., Local antibiotic therapy in osteomyelitis. Semin Plast Surg. May 2009;23(2):100-7.
Gong et al., Double-Network Hydrogels with Extremely High Mechanical Strength. Adv Mater. Jul. 17, 2003;15(14):1155-1158.
Gristina, Implant failure and the immuno-incompetent fibro-inflammatory zone. Clin Orthop Relat Res. Jan. 1994;(298):106-18.
Jahan et al., Combined chemical and mechanical effects on free radicals in UHMWPE joints during implantation. J Biomed Mater Res. Aug. 1991;25(8):1005-17.
Kashiwabara et al., Free Radicals and Crosslinking in Irradiated Polyethylene. Radiat Phys Chem. 1991;37(1):43-46.
Kobayashi et al., Preliminary study of polyvinyl alcohol-hydrogel (PVA-H) artificial meniscus. Biomaterials. Feb. 2003;24(4):639-47.
Maillard et al., Chimie Organique. Comptes Rendus Hebdomadaires Des Seances de L'Academie des Sciences. Jan. 8, 1912;154(2):66-68.
Mortin et al., Rapid bactericidal activity of daptomycin against methicillin-resistant and methicillin-susceptible *Staphylococcus aureus* peritonitis in mice as measured with bioluminescent bacteria. Antimicrob Agents Chemother. May 2007;51(5):1787-94.
Oral et al., A surface crosslinked UHMWPE stabilized by vitamin E with low wear and high fatigue strength. Biomaterials. Sep. 2010;31(27):7051-60.
Spellberg et al., Systemic antibiotic therapy for chronic osteomyelitis in adults. Clin Infect Dis. Feb. 1, 2012;54(3):393-407.
Stevens et al., An articulated antibiotic spacer used for infected total knee arthroplasty: a comparative in vitro elution study of Simplex and Palacos bone cements. J Orthop Res. Jan. 2005;23(1):27-33.
Suhardi et al., A Fully Functional Drug-Eluting Joint Implant. Nat Biomed Eng. 2017;1:0080.
Sutula et al., Impact of gamma sterilization on clinical performance of polyethylene in the hip. Clin Orthop Relat Res. Oct. 1995;(319):28-40.
Tanaka et al., Novel hydrogels with excellent mechanical performance. Progress in Polymer Science. Jan. 2005;30(1):1-9.
Thomas et al., The effect of dehydration history on PVA/PVP hydrogels for nucleus pulposus replacement. J Biomed Mater Res B Appl Biomater. May 15, 2004;69(2):135-40.
Van De Belt et al., Infection of orthopedic implants and the use of antibiotic-loaded bone cements. A review. Acta Orthop Scand. Dec. 2001;72(6):557-71.
Van De Belt et al., Surface roughness, porosity and wettability of gentamicin-loaded bone cements and their antibiotic release. Biomaterials. Oct. 2000;21(19):1981-7.
European Office Action for Application No. 07784150.0, dated Jan. 13, 2010, 6 pages.
European Office Action for Application No. 08829042.4, dated Dec. 23, 2010, 5 pages.
European Office Action, Response, for Application No. 08829042.4, dated Jul. 21, 2011, 14 pages.
International Search Report and Written Opinion for Application No. PCT/US2001/047507, dated Jul. 30, 2002, 4 pages.
International Search Report and Written Opinion for Application No. PCT/US2005/034662, dated Jan. 25, 2006, 11 pages.
International Search Report and Written Opinion for Application No. PCT/US2008/061250, dated Jul. 18, 2008, 7 pages.
International Search Report and Written Opinion for Application No. PCT/US2008/061388, dated Sep. 25, 2008, 6 pages.
International Search Report and Written Opinion for Application No. PCT/US2008/075252, dated Dec. 3, 2008, 11 pages.
International Search Report and Written Opinion for Application No. PCT/US2017/016506, dated Jul. 17, 2017, 10 pages.

\* cited by examiner

Figure 1. The schemical chemical structure of the liquid macromers.

Figure 2. Schematic depiction of an embodiment of the invention where the liquid polymerizable mixture is applied onto surface(s) of a femoral stem used in hip replacement surgery.

Figure 3. ¹H NMR for a liquid, polymerizable macromer made of PEG200 as the central, connecting moiety, DL-lactide as the biodegradable moiety and acrylate as the cross-linkable moiety with a molar ratio of 6:1 lactide to PEG units (61LP2 diac).

Figure 4. The photopolymerization of a liquid, polymerizable mixture containing gentamicin on UHMWPE and titanium surfaces.

Figure 5. The biodegradation of a representative biodegradable, drug-eluting hydrogel made according to this invention compared to bone cement.

Figure 6. The degradation (weight loss) profiles as a function of time for hydrogels polymerized using different formulations of liquid, macromer.

Figure 7. The concentration of gentamicin eluted into PBS at physiological conditions from a drug-eluting polymer prepared according to this invention compared to that from bone cement.

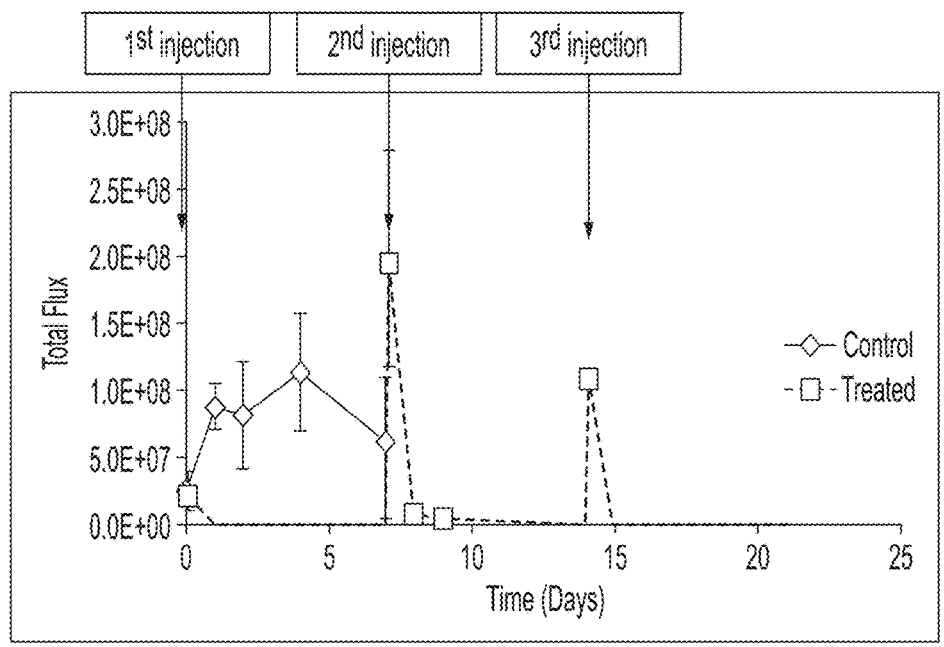

Figure 8 (b)

Figure 8. (a) Bioluminescent imaging of the control (titanium disc only) and Hydrogel (titanium disc covered with gentamycin eluting hydrogel on one side). Area inside the grey boxes indicates area where bioluminescence (presence of live bacteria) was observed. Absense of grey boxes in some pictures indicates absence of any bioluminescence. Color scale indicates total light flux received by the camera, the higher the light flux indicates higher amount of live bacteria. (b) Total bioluminescence flux vs time. Higher bioluminescence flux indicates higher live bacteria amount. $2^{nd}$ injection is performed at $2^{nd}$ week, while 3rd injection is performed at $3^{rd}$ week.

Figure 9 (a)

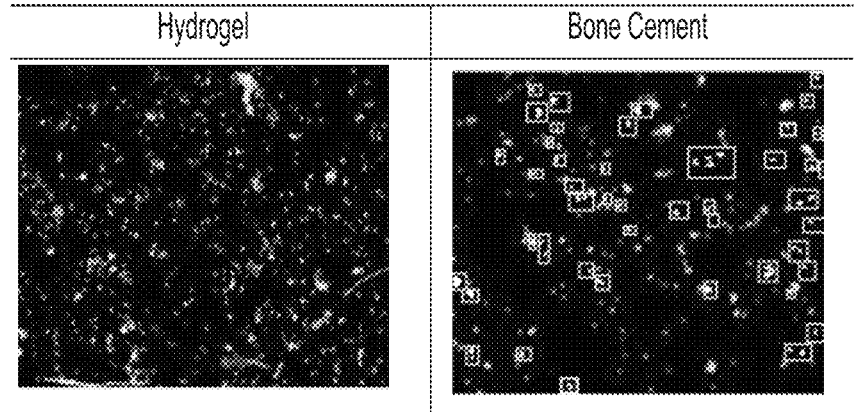

Figure 9 (b)

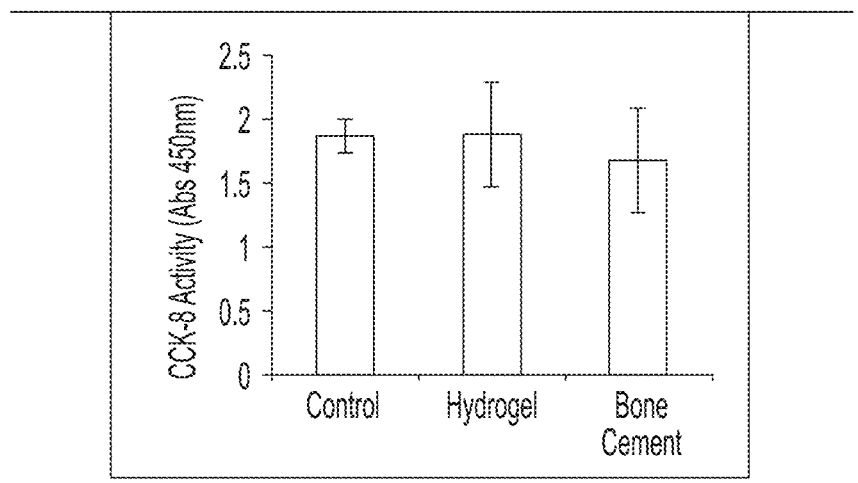

Figure 9. In Vitro Biocompatibility comparison of Hydrogel and Bone cement. (a) Live-Dead Fluorescence image of human macrophage grown on the surface of hydrogel and bone cement. White spots inside grey boxes indicate dead cells, while the remaining white spots are live cells. Cells on the surface of hydrogel were all alive, while notable amounts of dead cells were observed on the bone cement. (b) Quantification of number of live macrophages on the surface of hydrogel and bone cement through CCK-8 Activity. Control is cells in culture media (positive control).

Figure 10 (a)

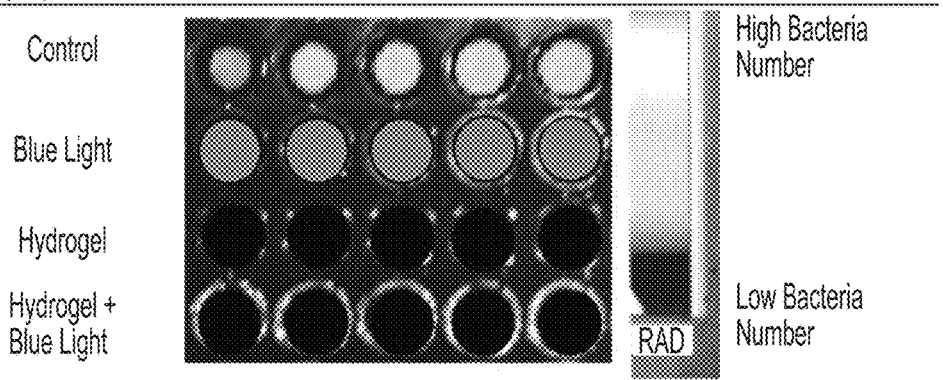

Figure 10 (b)

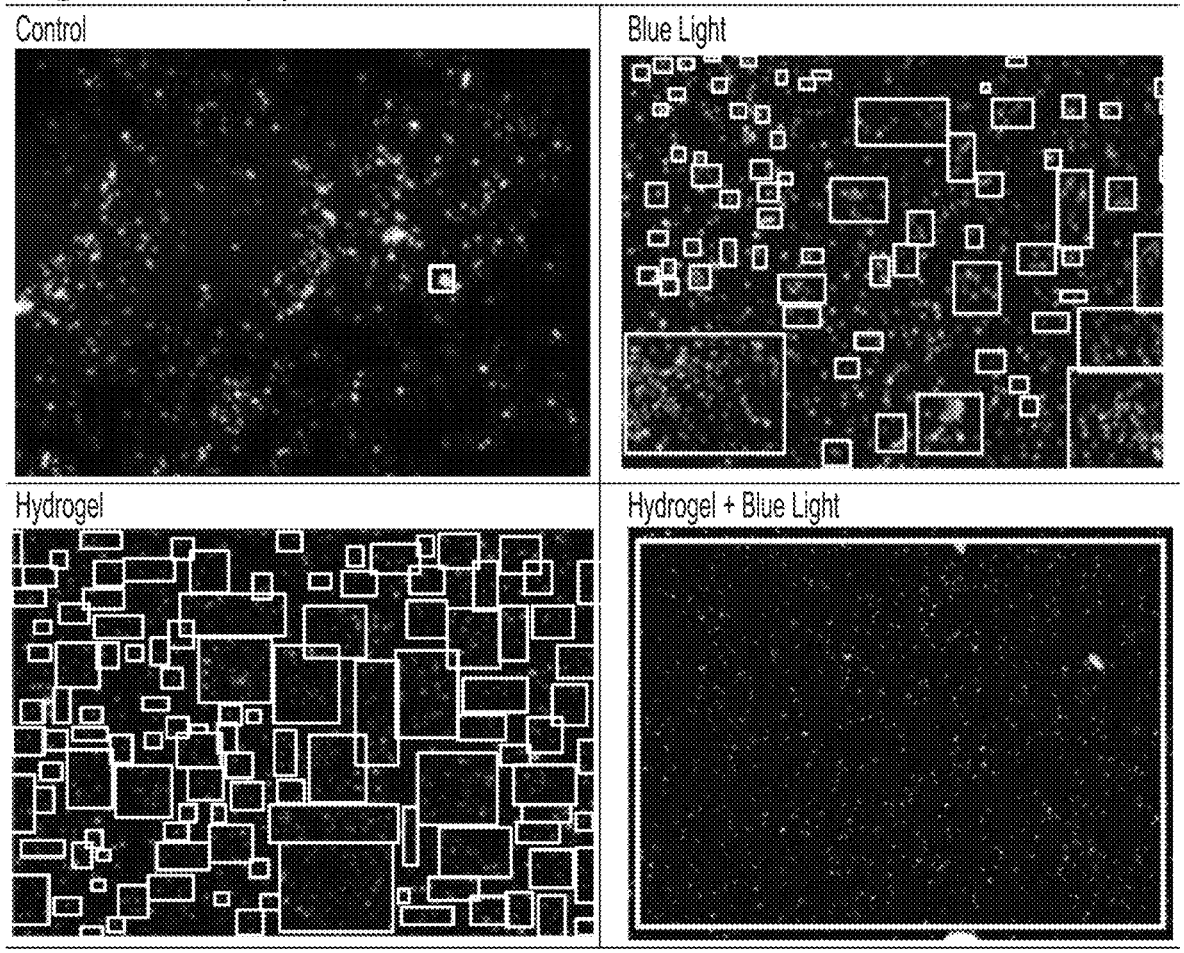

Figure 10. Antibacteria activity of hydrogel without antibiotics. (a) Bioluminescence imaging of bioluminescent bacterial culture exposed to nothing (control), blue light only, hydrogel only, and hydrogel+blue light. (b) live-dead fluorescence imaging of the bacterial culture exposed to nothing (control), blue light only, hydrogel only, and hydrogel+blue light. White spots in the grey boxes correspond to dead bacteria, while the remaining bacteria are alive.

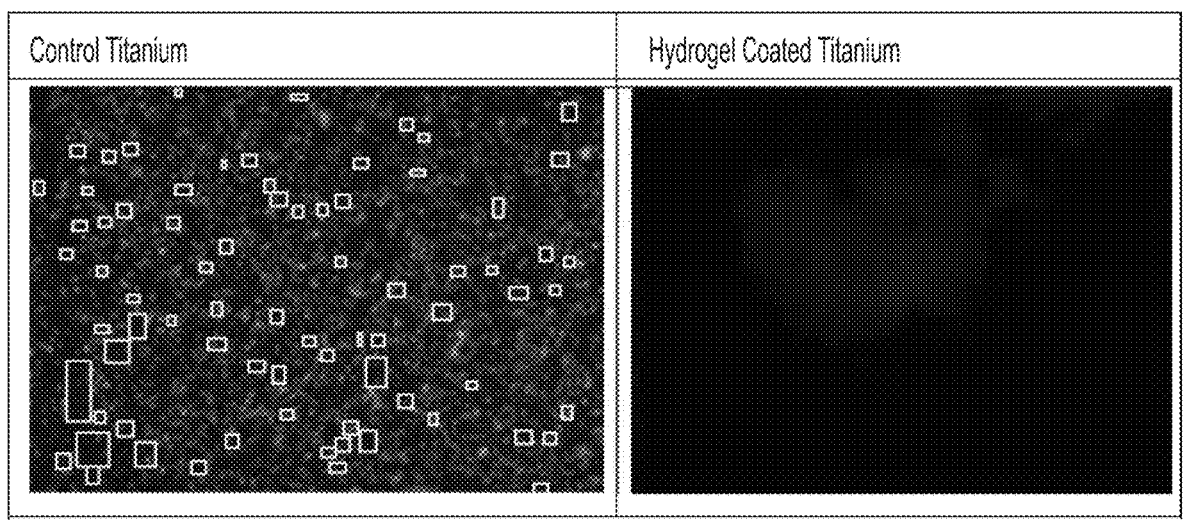
Figure 11. Biofilm formation on the plain titanium surface (control) and hydrogel coated titanium surface. White spots in the grey boxes indicated dead bacteria, while the remaining white spots were live bacteria. No white spots indicated absence of bacteria altogether.

Figure 12 (a)

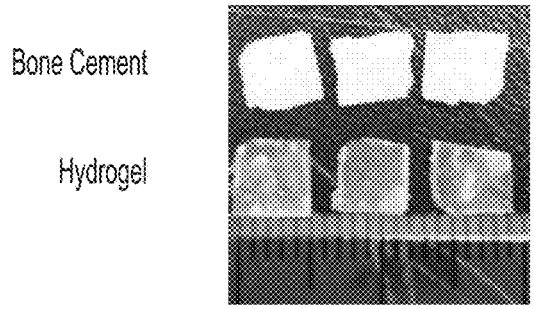

Figure 12 (b)

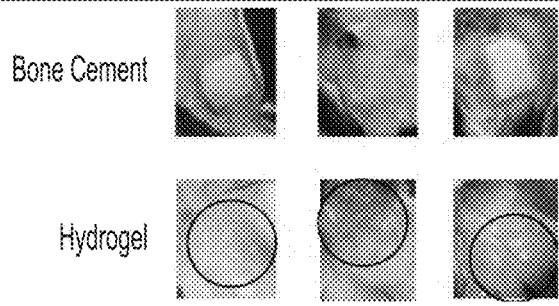

Figure 12 (c)

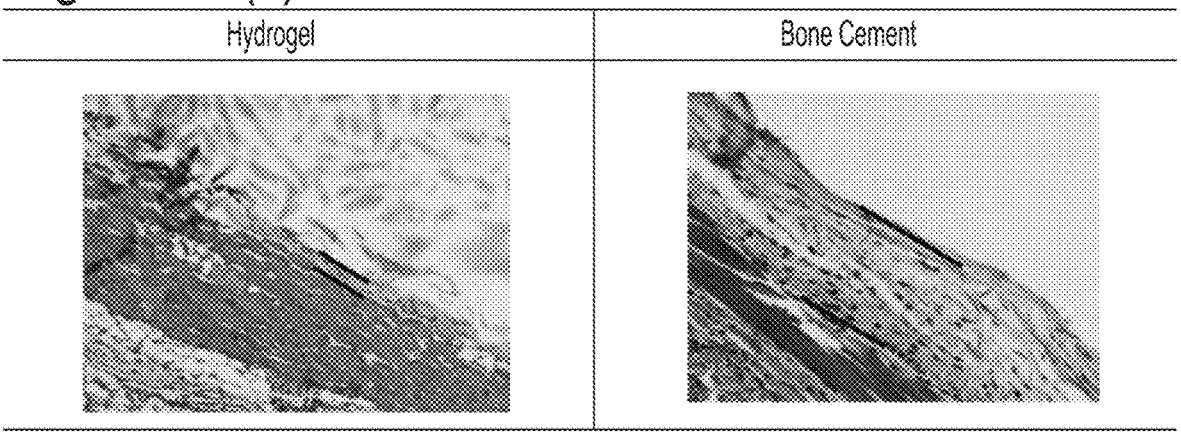

Figure 12. In vivo murine biocompatibility study of hydrogel and bone cement. (a) Bone cement and hydrogel discs before being implanted in the subcutaneous dorsal pocket of mice. (b) Bone cement and hydrogel discs explanted from the mice after one month of implantation. (c) Histology of interface between mice cutaneous tissues and hydrogel or bone cement. The area between two black lines indicate fibrous tissue. The area above the upper black line correspond to biodegraded hydrogel and former area of bone cement. Bone cement was removed prior to histology, therefore did not appear in the histology slide.

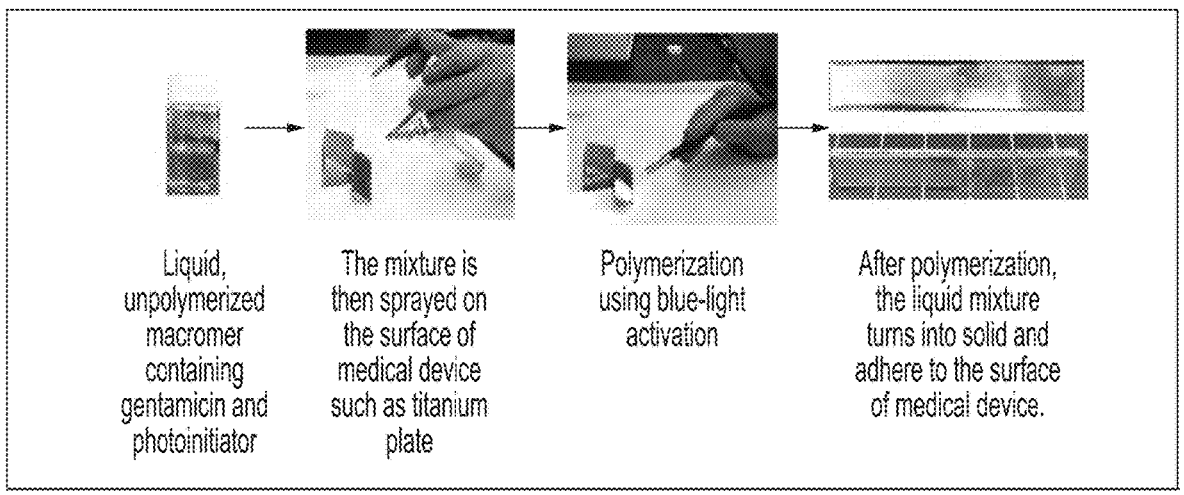
Figure 13. The photopolymerization of a liquid, polymerizable mixture containing gentamicin on titanium alloy (TiAl6V4).

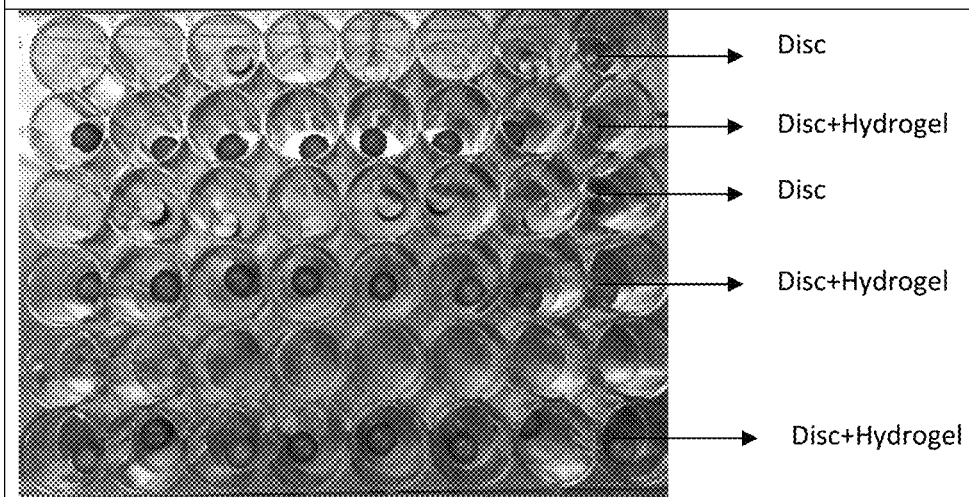

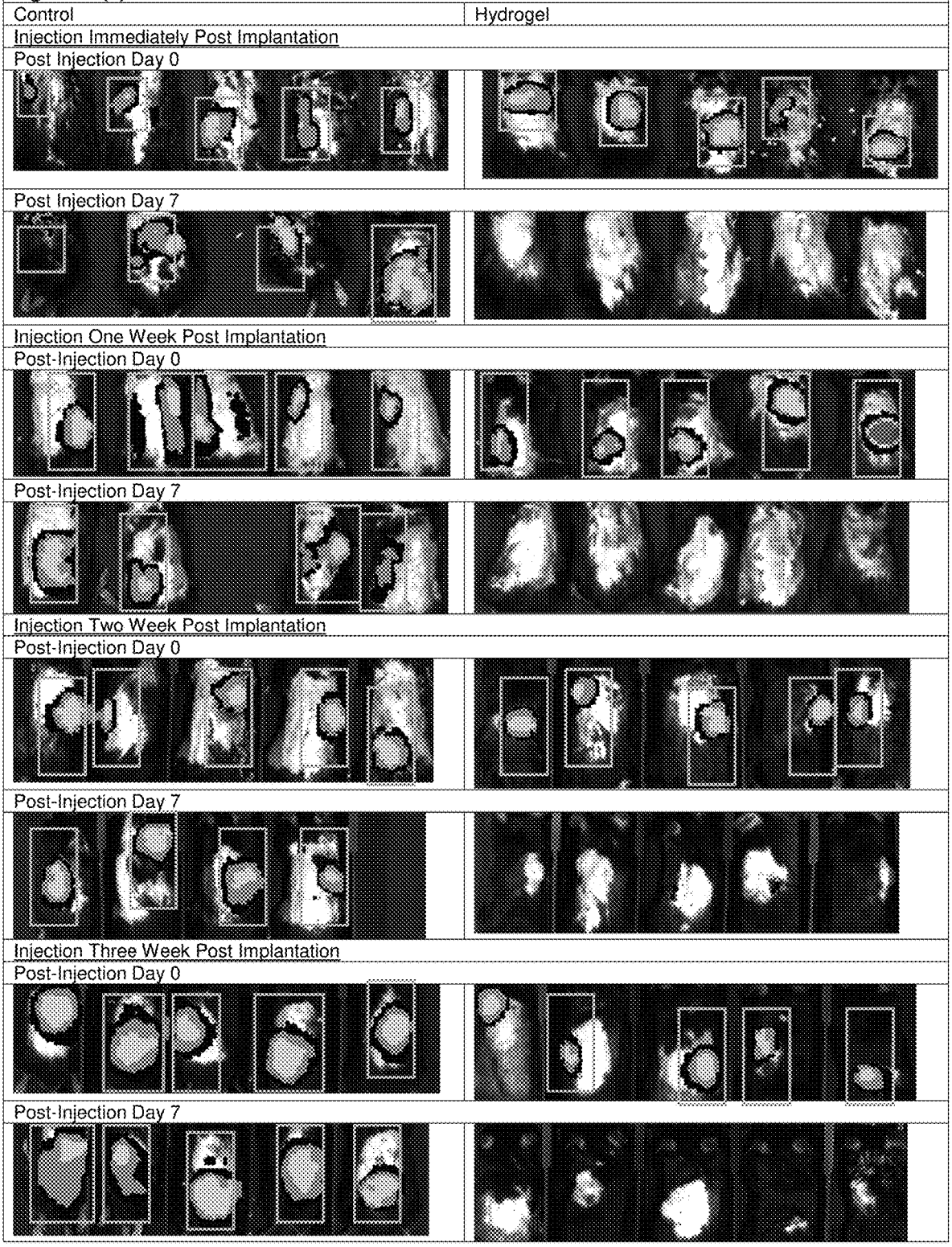

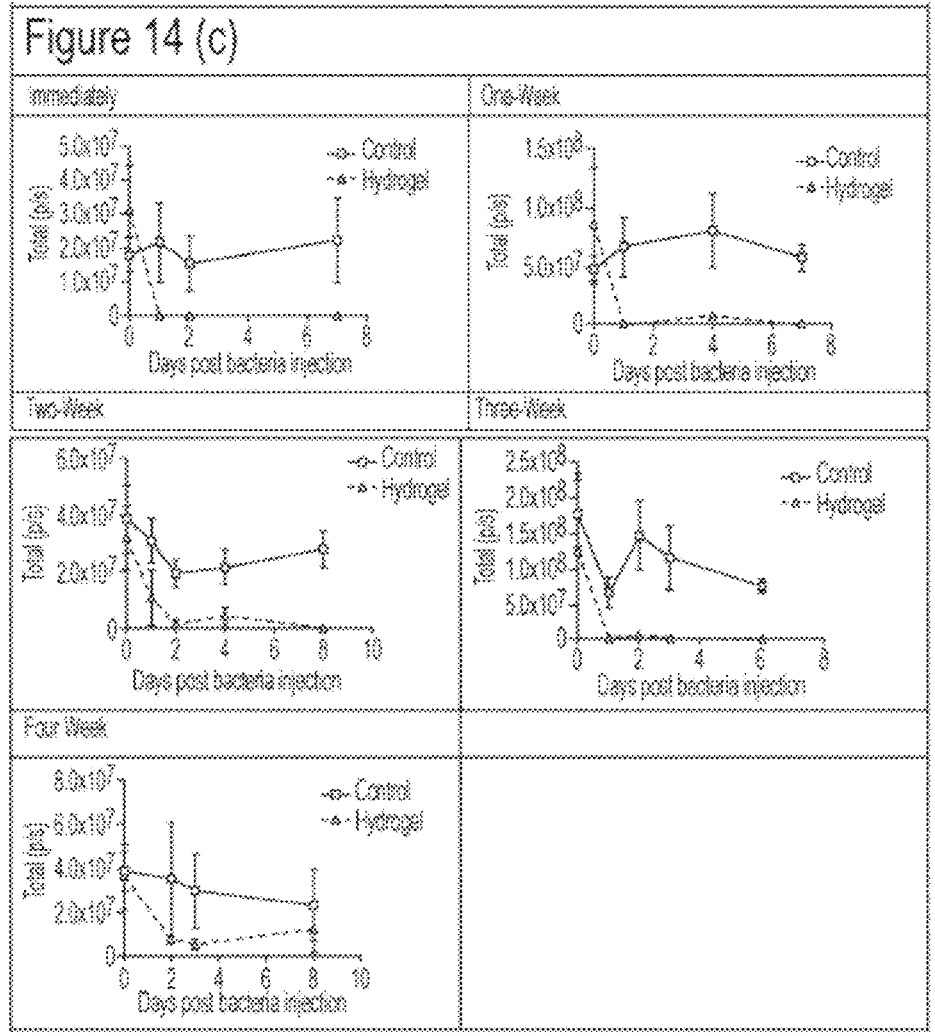

Figure 15 (a)

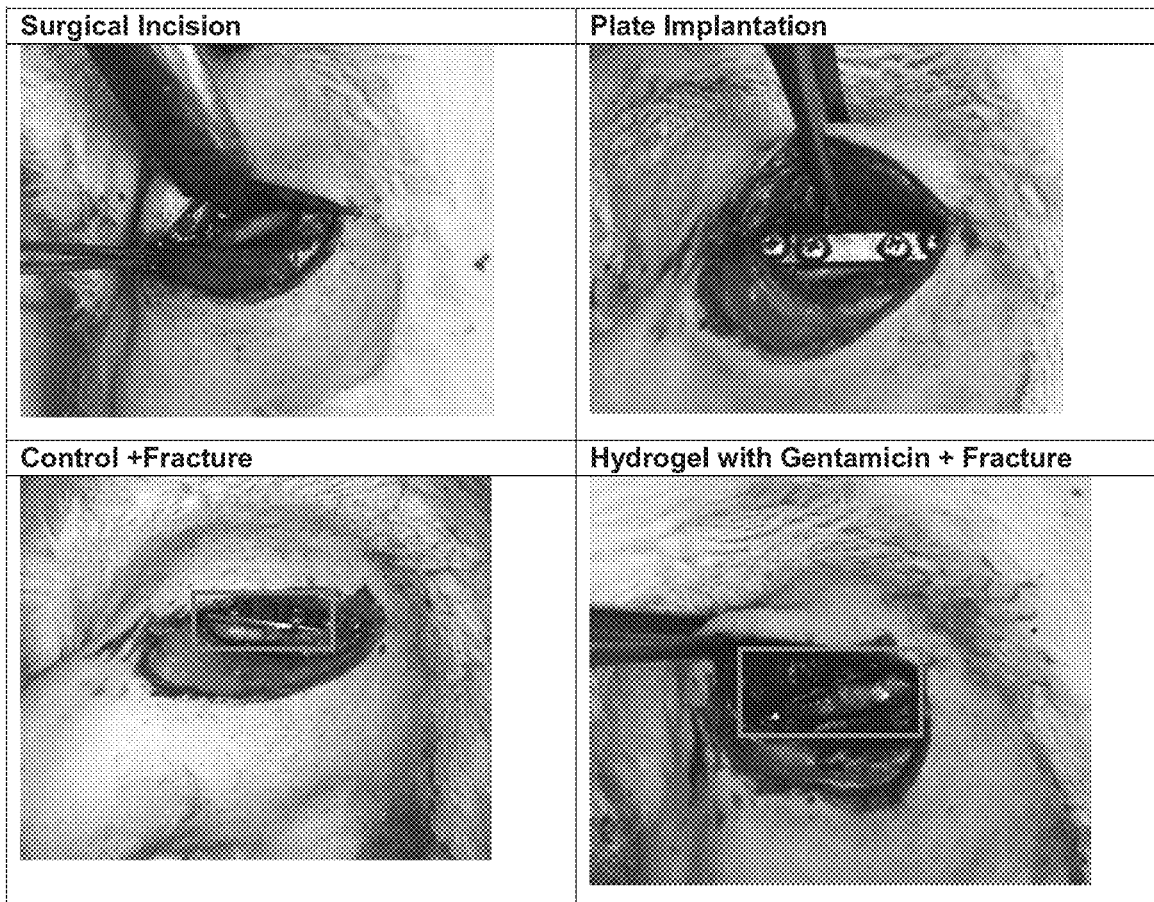

Figure 15 (b)

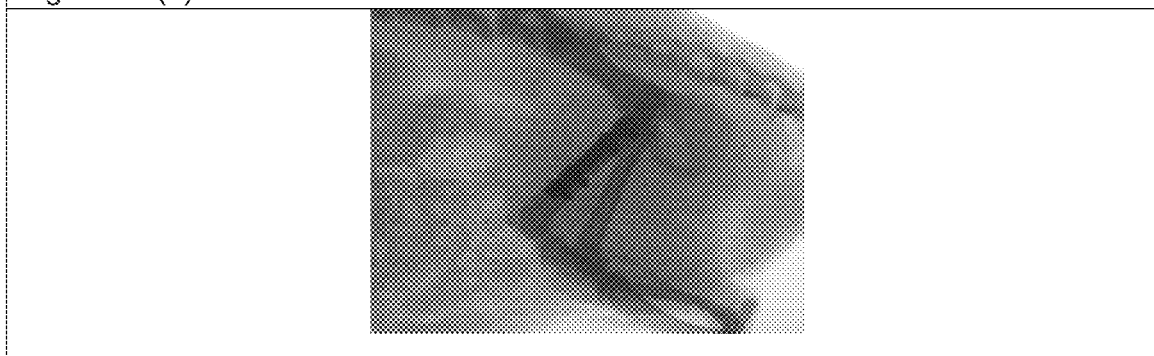

Figure 15. Surgical implantation of titanium only and titanium with hydrogel in femoral midshaft fracture model. (a) Upon incision and exposure of the lateral femur, either titanium or titanium coated with hydrogel containing gentamicin was implanted on the femur. A midshaft femoral fracture was then created. (b) Representative X-ray of implanted titanium plate on the mid-shaft fractured femur.

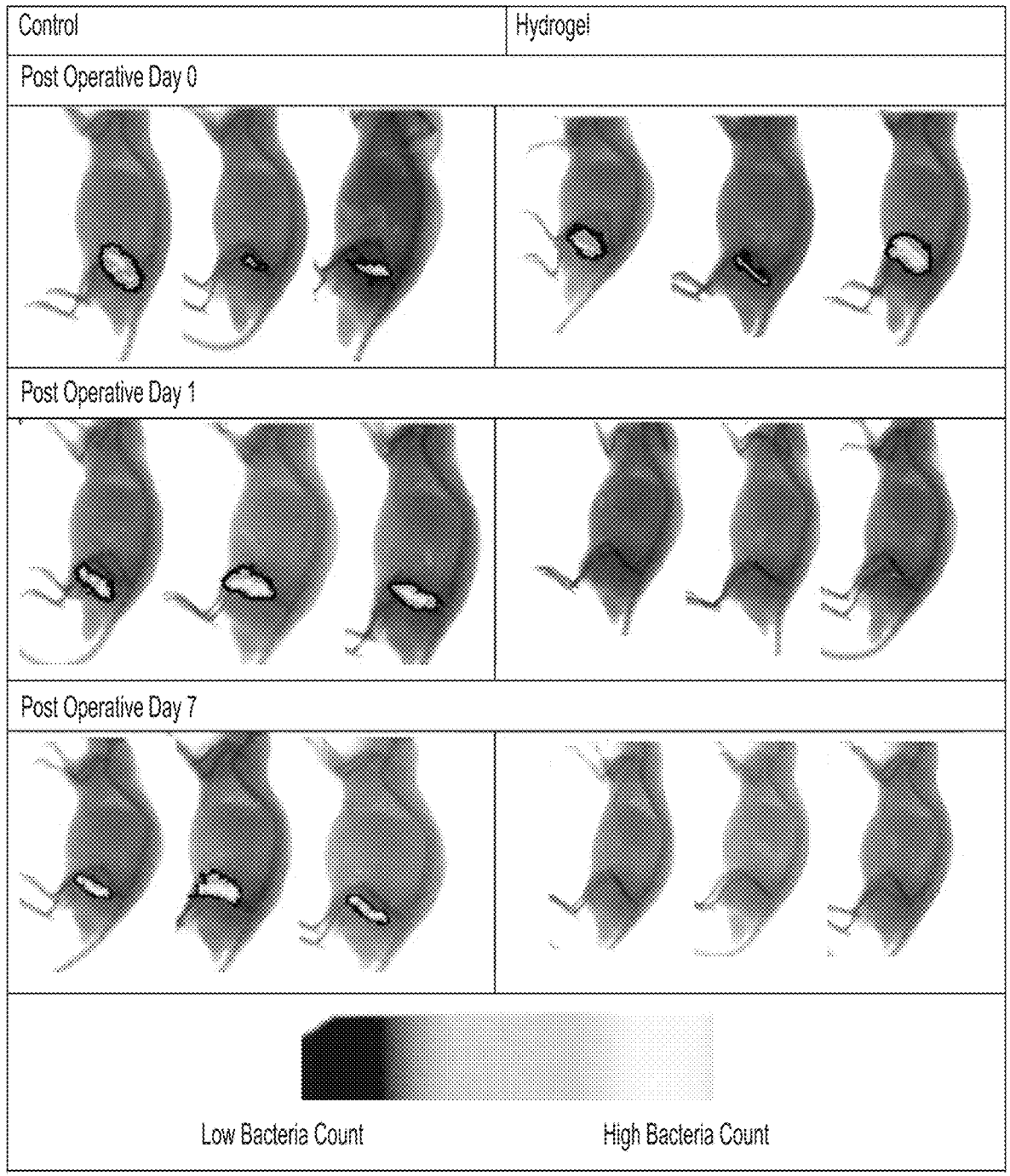
Figure 16. Bioluminescent imaging of the control (titanium plate only) and Hydrogel (titanium disc covered with gentamycin eluting hydrogel on one side). Color scale indicates total light flux received by the camera, the higher the light flux indicates higher amount of live bacteria.

Figure 17 (c)

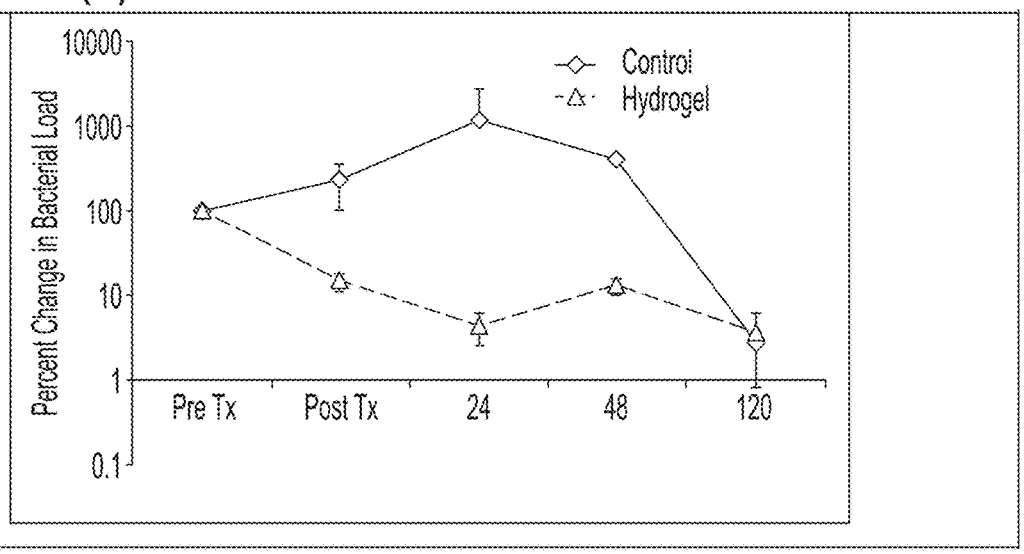

Figure 17. Application of hydrogel as antibacterial wound dressing and cover. (a) Representative image of surgical creation of full-thickness dermis wound on the mice dorsum. (b) Bioluminescent imaging of the control (tegaderm only) and Hydrogel covered wound. Color scale indicates total light flux received by the camera, the higher the light flux indicates higher amount of live bacteria. (c)

DRUG ELUTING POLYMER COMPOSED OF BIODEGRADABLE POLYMERS APPLIED TO SURFACE OF MEDICAL DEVICE

The present application is a 371 of International App. No. PCT/US2017/016506 filed Feb. 3, 2017, which claims the benefit of priority to U.S. Provisional App. No. 62/291,856 filed Feb. 5, 2016. The entire contents of the above-identified applications are hereby incorporated by reference.

This application claims priority to U.S. Provisional Application No. 62/291,856, filed Feb. 5, 2016, the contents of which are hereby incorporated by reference into this application.

FIELD OF THE INVENTION

This invention relates to drug eluting polymers. In particular, this invention provides biodegradable drug eluting polymers added to the surface of a medical device. The drug eluting polymer on the surface of the medical device is suitable to treat device associated complications and to deliver drug locally around the device. Device associated complications include but are not limited to infections, aseptic loosening, thrombosis, embolization, and immune reaction.

BACKGROUND OF THE INVENTION

Medical device associated infections are common complications that cause significant mortality and morbidity in patients. In the United States, it is estimated that annually 150,000 to 400,000 patients with bladder catheter or central venous catheter are infected respectively (Darouiche, R O. Device-Associated Infections: A Macroproblem that Starts with Microadherence. Clinical Infectious Diseases, 2001, 33:1567-1572). In the orthopedic field, 100,000 to 200,000 patients with fracture fixation devices, and 6,000 to 18,000 patients with joint prostheses are infected in U.S. annually. In the cardiovascular field, 5,000 to 23,000 patients with vascular grafts, 3,000 to 21,000 patients with cardiac pacemakers in US are infected annually. The actual rates of medical device associated infection might actually even be higher due to a variety of reasons, including increased rates of infection with re-implanted devices.

Medical devices have an increased susceptibility to bacterial colonization because of several factors. One reason is that; after implantation, the host immune system creates an immune-incompetent fibroinflammatory zone around the medical implant (Gristina A G. Implant failure and the immune-incompetent fibro-inflammatory zone. Clin Orthop Relat Res. 1994; 298:106-118). In addition, the biomaterial (s) used in manufacturing the medical device can induce adhesion of bacteria to the medical device. Adhesion of bacteria to the surface(s) of a medical device can then induce formation of bacterial biofilms that are much less accessible to antibiotics (Gristina A G. Implant failure and the immune-incompetent fibro-inflammatory zone. Clin Orthop Relat Res. 1994; 298:106-118).

Current treatment for medical device associated infections, e.g. prosthetic joints, pacemakers, fracture plates, intramedullary nails include removal of the device, debridement of potentially infected tissues surrounding the implants, reimplantation with new implants, and administration of systemic antibiotics. Alone, parenteral administration of antibiotics is not effective for treating medical device associated infections because the antibiotic penetration to the site of infection depends on the blood flow to the infected site. Areas with relatively low blood flow (e.g. bone, cartilage, immediate area surrounding medical implants) will have low local concentration of antibiotics, while areas with relatively high blood flow (e.g. liver, kidney) will have high concentration of antibiotics. For example, only 7-15% of intravenous cefazolin, 5-20% of intravenous vancomycin, and 5-19% of intravenous ceftriaxone penetrate bone (Spellberg B, Lipsky B A. Systemic Antibiotic Therapy for Chronic Osteomyelitis in Adults. Clin Infect Dis, 2012, 54(3):393-407). For infections associated with joint replacements, in addition to removal of the device and debridement of potentially infected tissues surrounding the implants, a spacer shaped like the articulating joint made of antibiotic-loaded bone cement is placed into the joint. In addition, systemic antibiotics are administered for at least 6 weeks (while the patient is immobilized), and a second surgery is performed for reimplantation with new implants.

Several drug eluting polymers, such as bone cements (PMMA-based in situ curing polymers) are available and in clinical use for the local delivery of antibiotics. For example, gentamicin containing bone cement that contains 1.0 gram gentamicin in a 40 g bone cement is commercially available under the trade name SmartSet® GHV Gentamicin, DePuy® CMW 2 Gentamicin, and Zimmer® Palacos R+G. Gentamicin containing bone cements can be used in total joint replacement both as prophylaxis or as treatment (Bourne R B. Prophylactic use of antibiotic bone cement an emerging standard-in the affirmative. J of Arthroplasty, 2004, 19(4), Suppl 1, 69-72). The gentamicin released from these bone cements reaches a maximum release rate of 10 $\mu g/cm^2/h$ shortly after implantation but decreases significantly to 0.1-1 $\mu g/cm^2/h$ by 24 hrs. and below 0.1 $\mu g/cm^2/hr$ by 1 week (Van de Belt H, Neut D, µges DRA, Schenk W, van Horn J R, van der Mei H C, Busscher H J. Surface roµghness, porosity and wettability of gentamicin-loaded bone cements and their antibiotic release. Biomaterials, 2000, 21:1981-1987). Because the amount of antibiotic eluted is very low after 24 hrs. the commercially available antibiotic cements are ineffective as a single mode of treatment for infection (Gogja J S, Meehan J P, Di Cesare, P, Jamali A A. Local Antibiotic Therapy in Osteomyelitis. Semin Plast Surg, 2009, 23(2):100-107). Clinical efficacy of antibiotic eluting bone cement as prophylaxis is inconclusive. A clinical study showed that antibiotic eluting bone cement in combination with systemic antibiotics are more effective in preventing deep hip infection than using either systemic antibiotics or antibiotic eluting bone cement alone in primary joint replacements (Espehaµg B, Engesaeter L B, Vollset S E, et al: Antibiotic prophylaxis in total hip Arthroplasty: Review of 10,905 primary cemented total hip replacements reported to the Norwegian Arthroplasty register, 1987-1995. J Bone Joint Surg Br 790:590, 1997). A clinical study of 3,000 patients using erythromycin and colistin-eluting bone cement did not show a decrease in the rate of infection when systemic prophylactic antibiotics were used.

Biodegradable antibacterial envelope TYRX™ is available for clinical use to reduce infection associated with pacemakers and implantable cardioverter defibrillators (http://www.tyrx.com/wcm/groups/mdtcom_sg/@mdt/@corp/documents/documents/uc201405268d-clinician-s-br.pdf). The biodegradable antibacterial envelope is composed of a bioabsorbable polacrylate polymer that elutes rifampin and minocycline. A clinical study of 1,129 patients showed 80% fewer major cardiac implantable electronic device infections as compared to the control cohort (0.44% vs 2.2%, p=0.0023) (http://www.tyrx.com/wcm/groups/mdtcom_sg/@mdt/@corp/documents/documents/uc201503789a_citadel_centurion.pdf).

A major drawback of most current commercially available drug eluting polymers are that they are pre-manufactured with the drug, and therefore medical professionals are unable to select the most specific drug for the patient and use the polymer to create a custom drug eluting polymer. Flexibility in using the desired drug or combination of drugs is desirable in applications such as when using antibiotics to treat peri-prosthetic implant infections. For effective doses of treatment drugs to be delivered, flexibility in manipulating drug elution rates and allowing effective dose delivery over desired periods of time is desirable. Biodegradability is desired because after all the drug has been eluted from a drug-eluting polymer, it could be a potential surface for colonization by bacteria and therefore susceptible to recurrent medical device infection.

SUMMARY OF THE INVENTION

The invention pertains to a liquid, polymerizable mixture of biodegradable macromonomer(s) (or macromers), which can be applied to the surface of a medical device and polymerized in situ. The liquid can be a macromer alone, or can contain initiators to allow different modes of in situ polymerization. The liquid can also contain inhibitor(s) to control the relative reaction rates of components during storage or use. The invention also pertains to methods of making the liquid, polymerizable mixture, adding bioactive agents and methods of applying said polymerizable mixture to the surface(s) of specific medical devices. The invention also pertains to drug-eluting polymers and methods of making them using liquid, polymerizable mixtures of biodegradable macromers.

An important aspect of the liquid mixture is that it is customizable by medical professionals such as doctors, nurses, emergency medical technicians to incorporate different bioactive agent(s) and applied to various surfaces of medical devices. Another important aspect of the drug eluting polymer is biodegradability. By biodegradation it is meant to include cleaving, destroying, or decomposing through hydrolysis, enzymatic degradation, biological modification by the liver, excretion by the kidney(s) and combinations of these modes of degradation. Biological modification by the liver means the changing of the chemical structure of the degraded polymer by the liver. As a result, the drug eluting polymer disappears in a certain period after implantation and therefore is no longer a potential surface for colonization by bacteria. Another important aspect of the described mixture is it can provide a liquid medium to allow solvation or dispersion of initiator(s) and/or inhibitor(s) and/or bioactive agent(s) without addition of any solvents. Another important aspect of the described mixture is that it can provide a liquid medium to allow the easy and diverse application of the mixture to a surface or surfaces of a medical device without the use of organic solvent(s).

The macromonomer or macromer mixture can be liquid, biodegradable, and cross-linkable at ambient conditions, at room temperature or at elevated temperatures. What is meant by room temperature is between about 0° C. and about body temperature or about 40° C. The cross-linking can also take place at temperatures higher than 40° C., for example at about 50° C., or at about 60° C., or higher. The macromer(s) are composed of a connecting moiety and biodegradable moiety and a cross-linkable moiety. In one embodiment, the macromer is composed of two biodegradable moieties connected by a central/connecting moiety and end capped with two or more cross-linkable moieties (FIG. 1). In this invention, most often a central connecting moiety is mentioned, but connecting moieties can be placed in between cross-linkable and biodegradable moieties as well. In another embodiment, the macromer is composed of one or more biodegradable moiety(ies) and end capped with two or more cross-linkable moiety(ies).

By connecting moiety, what is meant is a molecule(s) or part of a molecule that can be used to (upon one or more reactions) connect biodegradable moiety(ies) with biodegradable moiety(ies), biodegradable moiety(ies) with cross-linkable moiety(ies), and/or crosslinkable moiety(ies) with crosslinkable moiety(ies). Such connecting moieties can be chosen from but not limited to polyethylene glycol, polyethylene oxide, polypropylene glycol, 1,6-hexanediol, 2,2,6,6-Tetrakis(hydroxymethyl)cyclohexanol, ethylene glycol, or cyanuric acid. Such connecting moieties can be a mixture of different moieties and can consist of a mixture of different molecular weight distributions. Such connecting moieties can be homopolymers or random, alternating or block copolymers. In fact, in the current invention, there is always a distribution of molecular weights when describing any drug-eluting polymer or polymer mixture. In a preferred embodiment, the connecting moiety is a liquid at room temperature. By room temperature what is meant is between about 10° C. and 40° C. In one embodiment, the connecting moiety can be a mixture of polyethylene glycol and propylene glycol. In another embodiment, the connecting moiety can be mixture of polyethylene glycol with average molecular weight of 200 g/mol and polyethylene glycol with average molecular weight of 400 g/mol. In another embodiment, the connecting moiety can contain a distribution(s) of weight average molecular weight polyethylene glycol. In the preferred embodiment, the connecting moiety can be polyethylene glycol with weight average molecular weight of 200 g/mol (PEG 200). In another preferred embodiment, the connecting moiety can be polyethylene glycol with weight average molecular weight of 400 g/mol (PEG 400).

By biodegradable moiety, what is meant is a molecule or part of molecule that can be cleaved and/or destroyed and/or decomposed. The degradation can take place inside the body and the degradation byproducts can be eliminated by the body. The cleaving, destroying, or decomposing can be through hydrolysis, enzymatic degradation, modification by the liver, excretion by the kidney and/or combinations thereof. Modification by the liver means any process by which the polymerized liquid mixture or part of the polymer mixture are degraded as a result of contacting the liver. Such biodegradable moieties can be chosen from but not limited to poly(lactide) (PLA), poly(glycolide) (PGA), poly(epsilon-caprolactone) (PCA), poly(dioxane) (PDA), poly(trimethylene carbonate) (PTMC), and combinations thereof. In one embodiment, the biodegradable moiety is polyglycolide. In order to arrive at the resultant moiety in the macromer to be polymerized, pre-cursor molecules can be used such as the monomers of said polymeric moieties. In another embodiment, copolymers or said moieties can be used. In another embodiment, the biodegradable moiety is polylactide-co-polyglycolide. In another embodiment, the biodegradable moiety is polytrimethylene carbonate-co-poly(epsilon-caprolactone). The degree of polymerization of the biodegradable moieties can be modulated to keep the resulting macromer liquid at room temperature. In a preferred embodiment, the biodegradable moiety is polylactide with 1 to 8 or more lactoyl groups. In another preferred embodiment, the biodegradable moiety is polyglycolide with 1 to 8 or more glycolyl groups. In another preferred embodiment, the biodegradable moiety is polycaprolactone with 1 to 8 or more epsilon-caprolactone groups. In an even more preferred embodiments, the biodegradable moiety is polylactide with 2 to 4 lactoyl groups.

By cross-linkable moiety, what is meant is a molecule or part of a molecule that can form one or more new bond(s) (covalent and/or non-covalent) with another molecule, for example as part of a macromer to create a network of molecule(s) and/or macromers. Such crosslinkable moieties can be chosen from but are not limited to acrylates, methacrylates, thiols, carboxyls, hydroxyls, amino groups, isocyanates, azides, isothiocyanates, epoxides, and/or combinations thereof. In a preferred embodiment the cross-linkable moiety is chosen from acrylate(s), methacrylate(s), or combinations thereof. In a more preferred embodiment, the cross-linkable moiety contains an acrylate group. One or more cross-linkable moieties can be used to prepare a mixture of liquid macromers with different reactivity to external stimulation for subsequent polymerization. Multifunctional cross-linkable moieties (moieties that can bond to more than two molecules) can be used to create different networks. In addition, some of these cross-linkable moieties can be used to bond the polymerizable mixture onto the applied surface(s) of medical devices before, during or after polymerization of the liquid, polymerizable mixture.

In some embodiments, the formulation used to create drug-eluting polymer(s) is composed of a liquid, polymerizable macromer or macromer mixture and additive(s). Mixture(s) and additive(s) can be pre-mixed or mixed at the time of application. Additive(s) can be bioactive agent(s), initiator(s), inhibitor(s) in any composition or concentration. Non-reactive additive(s) can also be used to change the reactivity or the viscosity of the said mixture. In a preferred embodiment, the liquid, polymerizable mixture is composed of a macromer, an initiator, and an inhibitor. In another preferred embodiment, the mixture is composed of a macromer and an inhibitor. In another preferred embodiment, the mixture is composed of a macromer, an initiator, an inhibitor, and one or more bioactive agent(s).

In a preferred embodiment the additive is a mixture of initiator and bioactive agent. In another preferred embodiment, the additive is a mixture of initiator, inhibitor, and bioactive agent. The addition of bioactive agent(s) or drug(s) to the macromonomer is to subsequently deliver the bioactive agent(s) or the drug(s) from the drug eluting polymer. The use of initiator is to initiate polymerization of the macromonomer(s). The use of inhibitor is to prevent unintentional polymerization of the macromonomer(s).

The liquid macromonomer or macromer mixture can be self-crosslinking; that is, it can have a finite polymerization rate without mixing with an initiator. To slow down or hinder this finite rate of polymerization, an inhibitor can be added to the liquid macromer after formulation.

In a preferred embodiment, the liquid polymerizable mixture with additive(s) is polymerized upon providing an external stimulus in the presence of a polymerization initiator.

In a preferred embodiment, an inhibitor is mixed with the macromer upon formulation to prevent unintentional polymerization. In another embodiment the inhibitor is mixed with the macromer, initiator and/or bioactive agent to prevent unintentional polymerization. In the preferred embodiment the inhibitor is hydroquinone.

BRIEF DESCRIPTION OF THE DRAWINGS

FIG. 8 (a) depicts bioluminescent imaging of the control (titanium disc only) and Hydrogel (titanium disc covered with gentamycin eluting hydrogel on one side). Area inside the grey boxes indicates area where bioluminescence (presence of live bacteria) was observed. Absence of grey boxes in some pictures indicates absence of any bioluminescence. Color scale indicates total light flux received by the camera, the higher the light flux indicates higher amount of live bacteria. FIG. 8 (b) is a graph depicting total bioluminescence flux vs time. Higher bioluminescence flux indicates higher live bacteria amount. 2nd injection is performed at 2nd week, while 3rd injection is performed at 3rd week.

FIGS. 9 (a) and 9 (b) depict in vitro biocompatibility comparison of hydrogel and bone cement. FIG. 9 (a) depicts Live-Dead Fluorescence image of human macrophage grown on the surface of hydrogel and bone cement. White spots inside grey boxes indicate dead cells, while the remaining white spots are live cells. Cells on the surface of hydrogel were all alive, while notable amounts of dead cells were observed on the bone cement. FIG. 9 (b) is a graph depicting quantification of number of live macrophages on the surface of hydrogel and bone cement through CCK-8 Activity. Control is cells in culture media (positive control).

FIGS. 10 (a) and 10 (b) depict antibacterial activity of hydrogel without antibiotics. FIG. 10 (a) depicts bioluminescence imaging of bioluminescent bacterial culture exposed to nothing (control), blue light only, hydrogel only, and hydrogel+blue light. FIG. 10 (b) depicts live-dead fluorescence imaging of the bacterial culture exposed to nothing (control), blue light only, hydrogel only, and hydrogel+blue light. White spots in the grey boxes correspond to dead bacteria, while the remaining bacteria are alive.

FIG. 11 depicts biofilm formation on the plain titanium surface (control) and hydrogel coated titanium surface. White spots in the grey boxes indicated dead bacteria, while the remaining white spots were live bacteria. No white spots indicated absence of bacteria altogether.

FIGS. 12 (a), 12 (b) and 12 (c) depict in vivo murine biocompatibility study of hydrogel and bone cement. FIG. 12 (a) depicts bone cement and hydrogel discs before being implanted in the subcutaneous dorsal pocket of mice. FIG. 12 (b) depicts bone cement and hydrogel discs explanted from the mice after one month of implantation. FIG. 12 (c) depicts histology of interface between mice cutaneous tissues and hydrogel or bone cement. The area between two black lines indicate fibrous tissue. The area above the upper black line correspond to biodegraded hydrogel and former area of bone cement. Bone cement was removed prior to histology, therefore did not appear in the histology slide.

FIG. 13 schematically depicts the photopolymerization of a liquid, polymerizable mixture containing gentamicin on titanium alloy (TiAl6V4).

FIGS. 14 (a), 14 (b) and 14 (c) depict long term in vivo antibacterial activity of gentamicin eluting hydrogel exposed to repeated bacterial injection. FIG. 14 (a) depicts titanium discs (control) and titanium discs covered with gentamicin eluting hydrogel (hydrogel) before being implanted. FIG. 14 (b) depicts bioluminescent imaging of the control (titanium disc only) and Hydrogel (titanium disc covered with gentamycin eluting hydrogel on one side). Area inside the grey boxes indicates area where bioluminescence (presence of live bacteria) was observed. Absence of grey boxes in some pictures indicates absence of any bioluminescence. FIG. 14 (c) depicts graphs showing total bioluminescence flux vs time. Higher bioluminescence flux indicates higher live bacteria amount.

FIGS. 15 (a) and 15 (b) depict surgical implantation of titanium only and titanium with hydrogel in femoral mid-shaft fracture model. FIG. 15 (a) depicts, upon incision and exposure of the lateral femur, either titanium or titanium coated with hydrogel containing gentamicin was implanted on the femur. A midshaft femoral fracture was then created. FIG. 15 (b) depicts a representative X-ray of implanted titanium plate on the mid-shaft fractured femur.

FIG. 16 depicts bioluminescent imaging of the control (titanium plate only) and Hydrogel (titanium disc covered with gentamycin eluting hydrogel on one side). Scale indicates total light flux received by the camera, the higher the light flux indicates higher amount of live bacteria.

FIG. 17 (a) depicts a representative image of surgical creation of full-thickness dermis wound on the mice dorsum. FIG. 17 (b) depicts bioluminescent imaging of the control (tegaderm only) and Hydrogel covered wound. Scale indicates total light flux received by the camera, the higher the light flux indicates higher amount of live bacteria. FIG. 17 (c) is a graph depicting percent change in bacterial load as measured before and after the bacterial injection, and also at 24 hr, 48 hr, and 120 hr.

DETAILED DESCRIPTION OF THE EMBODIMENTS

Figure 1:
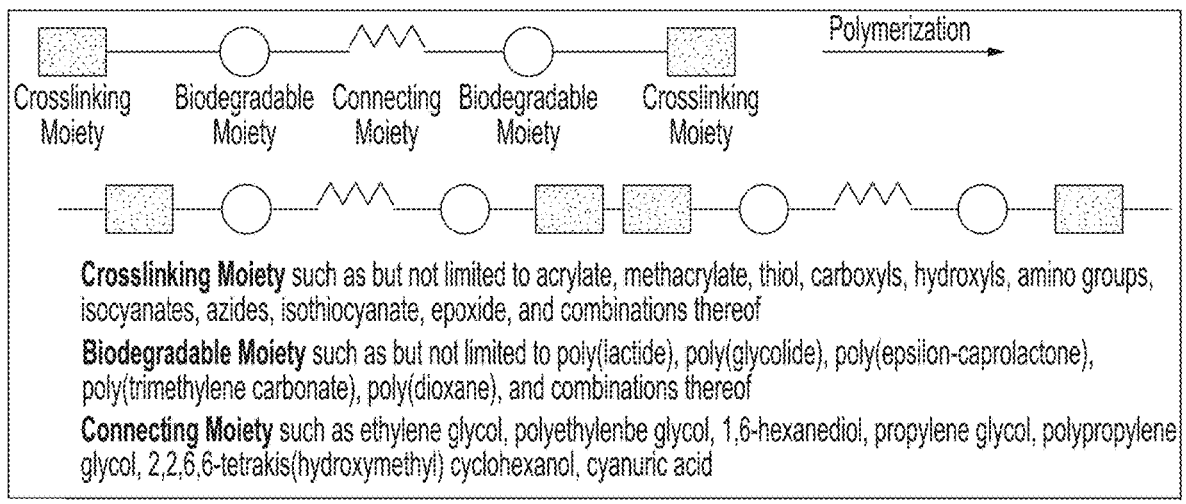
FIG. 1 schematically depicts the chemical structure of the liquid macromers.

Described herein is a liquid, polymerizable mixture comprising a composition of liquid, biodegradable, and cross-linkable macromers or macromonomers. Such a mixture can also contain a polymerization initiator to initiate the polymerization under desired external stimuli such as visible light, UV light or thermal treatment such as heating. Such a mixture can also contain at least one bioactive agent such as an antibiotic. Upon partial or complete polymerization after being stimulated by one or more external stimuli, the liquid, polymerizable mixture is transformed into a solid polymer, which is capable of eluting one or more bioactive agents contained within when in contact with an eluting environment. Before polymerization, the liquid, polymerizable mixture can be applied to the surface or surfaces of a medical device and the polymerization can be accomplished on the surfaces of the medical device.

The present invention provides methods of making a drug-eluting polymer comprising: (i) formulating a liquid, polymerizable mixture composed of liquid, biodegradable and crosslinkable macromer(s) and also initiator(s) and bioactive agent(s); (ii) applying the liquid, polymerizable mixture on the surface or surfaces of a medical device; (iii) providing an external stimulus to initiate polymerization and (iv) providing time for polymerization; thereby forming a drug-eluting polymer.

The present invention provides methods of making a liquid, polymerizable macromer or a mixture of macromers by (i) taking a connecting moiety (optionally central); (ii) covalently bonding one or more biodegradable moieties to the connecting moiety; and (iii) covalently bonding one or more cross-linking moieties to the biodegradable moieties bonded to the connecting moiety (optionally, a central connecting moiety); thereby forming a liquid, polymerizable macromer or a mixture of macromers. A mixture of such macromers can be formulated also by performing steps (i) through (iii) using different components and mixing resultant, individual liquid, biodegradable, crosslinkable macromers.

The present invention provides methods of making drug-eluting polymers comprising providing a liquid polymerizable mixture comprising at least a macromer, which is a liquid between about 0° C. and about 40° C., made by covalently linking a connecting moiety (optionally, a central connecting moiety) by biodegradable moieties and covalently bonding cross-linkable moieties to the biodegradable moieties; and at least one initiator; mixing with at least one bioactive agent; forming a liquid, bioactive agent-containing polymerizable mixture; initiating polymerization by an external stimulus; polymerizing for a period of time; thereby forming a drug-eluting polymer.

The present invention provides methods of making drug-eluting polymers comprising providing a liquid polymerizable mixture comprising at least a macromer, which is a liquid between about 10° C. and about 40° C., made by covalently linking a connecting moiety (optionally, a central connecting moiety) by biodegradable moieties and covalently bonding cross-linkable moieties to the biodegradable moieties; and at least one initiator; mixing with at least one bioactive agent; forming a liquid, bioactive agent-containing polymerizable mixture; applying the liquid, polymerizable mixture onto at least one surface of a medical device; initiating polymerization by an external stimulus; polymerizing for a period of time; thereby forming a drug-eluting polymer.

In an embodiment, the invention provides a method of making a drug-eluting polymer comprising: (i) providing a liquid, polymerizable mixture composed of liquid, biodegradable and cross-linkable macromer(s) and also initiator(s) and bioactive agent(s); (ii) applying an adhesive onto the surface or surfaces of a medical device; (iii) applying the liquid, polymerizable mixture on the surface or surfaces of a medical device previously contacted with adhesive; (iii) providing an external stimulus to initiate polymerization and (iv) providing time for polymerization; thereby forming a drug-eluting polymer.

In a preferred embodiment, the invention provides a method of making a drug-eluting polymer comprising: (i) providing a liquid, polymerizable mixture composed of liquid, biodegradable and cross-linkable macromer(s) and also initiator(s) and an antibiotic; (ii) applying the liquid, polymerizable mixture on the surface or surfaces of a medical device previously contacted with adhesive; (iii)

providing an external stimulus to initiate polymerization and (iv) providing time for polymerization; thereby forming a drug-eluting polymer.

In an embodiment, the invention provides a method of making a drug-eluting polymer comprising: providing a liquid polymerizable mixture comprising at least a macromer that is a liquid at a temperature between about 0° C. and about 40° C., wherein the liquid polymerizable mixture is made by covalently linking a connecting moiety to at least one biodegradable moiety and covalently linking at least one cross-linkable moiety to the biodegradable moiety (sequentially or simultaneously, in the order desired); and at least one initiator; mixing with at least one bioactive agent; forming a liquid, bioactive agent-containing polymerizable mixture; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising at least a macromer that is a liquid at a temperature between about 10° C. and about 40° C., wherein the liquid polymerizable mixture is made by covalently linking a connecting moiety to at least one biodegradable moiety and covalently linking at least one cross-linkable moiety to the biodegradable moiety (sequentially or simultaneously, in the order desired); and at least one initiator; mixing with at least one bioactive agent; forming a liquid, bioactive agent-containing polymerizable mixture; applying the liquid, polymerizable mixture onto at least one surface of a medical device; initiating polymerization by an external stimulus; polymerizing for a period of time; thereby forming a drug-eluting polymer. Yet in another embodiment, the liquid polymerizable mixture is made by covalently linking a connecting moiety to biodegradable moieties and covalently linking cross-linkable moieties to the biodegradable moieties (sequentially or simultaneously, in the order desired); and at least one initiator.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin; forming a liquid, bioactive agent-containing polymerizable mixture; applying the liquid, polymerizable mixture onto a fracture plate; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin; forming a liquid, bioactive agent-containing polymerizable mixture; applying the liquid, polymerizable mixture onto the surface(s) of an acetabular shell, acetabular cup or femoral stem of a total hip replacement implant; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin; forming a liquid, bioactive agent-containing polymerizable mixture; applying the liquid, polymerizable mixture onto the surface(s) of femoral or tibial component or patellar component of a total knee replacement implant; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin and rifampin; forming a liquid, bioactive agent-containing polymerizable mixture; applying the liquid, polymerizable mixture onto an internal fixation (fracture) plate; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin and rifampin; forming a liquid, bioactive agent-containing polymerizable mixture; applying the liquid, polymerizable mixture onto the surface(s) of an acetabular shell, acetabular cup or femoral stem of a total hip replacement implant; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin and rifampin; forming a liquid, bioactive agent-containing polymerizable mixture; applying the liquid, polymerizable mixture onto the surface(s) of femoral or tibial component or patellar component of a total knee replacement implant; initiating polymerization by an external stimulus; polymerizing for a period of time; thereby forming a drug-eluting polymer. Yet in another embodiment, the liquid polymerizable mixture is made by covalently linking a polyethylene glycol moiety of a molecular weight below 1000 g/mol to biodegradable lactide moieties and covalently linking cross-linkable acrylate moieties to the lactide moieties (sequentially or simultaneously, in the order desired); and at least one initiator.

In another embodiment, the invention provides a method of making a polymer comprising: providing a liquid polymerizable mixture comprising at least a macromer that is a liquid at a temperature between about 0° C. and about 40° C., wherein the liquid polymerizable mixture is made by covalently linking a connecting moiety to at least one biodegradable moiety and covalently linking at least one cross-linkable moiety to the biodegradable moiety (sequentially or simultaneously, in the order desired); and at least one initiator; initiating polymerization by an external stimulus; polymerizing for a period of time; thereby forming a polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with at least one bioactive agent; forming a liquid, bioactive agent-containing polymerizable mixture; applying the liquid, polymerizable mixture; initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with at least one bioactive agent; forming a liquid, bioactive agent-containing polymerizable mixture; applying the liquid, polymerizable mixture on tissue allograft(s); initiating polymerization by an external stimulus; polymerizing for a period of time; thereby forming a drug-eluting polymer.

In another embodiment, the invention provides a method of making a drug-eluting polymer comprising: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with gentamicin; forming a liquid, bioactive agent-containing polymerizable mixture; applying the liquid, polymerizable mixture onto fixation devices including fracture plates and associated pins and screws; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising at least a macromer that is a liquid at a temperature between about 0° C. and about 40° C., wherein the liquid polymerizable mixture is made by covalently linking a connecting moiety to at least one biodegradable moiety and covalently linking at least one cross-linkable moiety to the biodegradable moiety (sequentially or simultaneously, in the order desired); and at least one initiator; mixing with at least one bioactive agent; forming a liquid, bioactive agent-containing polymerizable mixture; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising at least a macromer that is a liquid at a temperature between about 10° C. and about 40° C., wherein the liquid polymerizable mixture is made by covalently linking a connecting moiety to at least one biodegradable moiety and covalently linking at least one cross-linkable moiety to the biodegradable moiety (sequentially or simultaneously, in the order desired); and at least one initiator; mixing with at least one bioactive agent; forming a liquid, bioactive agent-containing polymerizable mixture; applying the liquid, polymerizable mixture onto at least one surface of a medical device; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin; forming a liquid, bioactive agent-containing polymerizable mixture; applying the liquid, polymerizable mixture onto a fracture plate; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin; forming a liquid, bioactive agent-containing polymerizable mixture; applying the liquid, polymerizable mixture onto the surface(s) of an acetabular shell, acetabular cup or femoral stem of a total hip replacement implant; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin; forming a liquid, bioactive agent-containing polymerizable mixture; applying the liquid, polymerizable mixture onto the surface(s) of femoral or tibial component or patellar component of a total knee replacement implant; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin and rifampin; forming a liquid, bioactive agent-containing polymerizable mixture; applying the liquid, polymerizable mixture onto an internal fixation (fracture) plate; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin and rifampin; forming a liquid, bioactive agent-containing polymerizable mixture; applying the liquid, polymerizable mixture onto the surface(s) of an acetabular shell, acetabular cup or femoral stem of a total hip replacement implant; initiating polymerization by an external stimulus; polymerizing for a period of time; thereby forming a drug-eluting polymer.

In another embodiment, the invention provides a drug-eluting polymer composition made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with vancomycin and rifampin; forming a liquid, bioactive agent-containing polymerizable mixture; applying the liquid, polymerizable mixture onto the surface(s) of femoral or tibial component or patellar component of a total knee replacement implant; initiating polymerization by an external stimulus; polymerizing for a period of time; thereby forming a drug-eluting polymer.

In another embodiment, the invention provides a drug-eluting polymer composition comprising: a liquid polymerizable mixture comprising at least a macromer that is a liquid at a temperature between about 0° C. and about 40° C., wherein the liquid polymerizable mixture comprises a connecting moiety covalently linked to at least one biodegradable moiety, which is covalently linked to at least one cross-linkable moiety to the biodegradable moiety, and at least one initiator.

In another embodiment, the invention provides a drug-eluting polymer composition comprising: a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety, and at least one initiator.

In another embodiment, the invention provides a polymer comprising made by a process comprising the steps of: providing a liquid polymerizable mixture comprising at least a macromer that is a liquid at a temperature between about 0° C. and about 40° C., wherein the liquid polymerizable mixture is made by covalently linking a connecting moiety to at least one biodegradable moiety and covalently bonding to at least one cross-linkable moiety to the biodegradable moiety (sequentially or simultaneously, in the order desired); and at least one initiator; initiating polymerization by an external stimulus; polymerizing for a period of time; thereby forming a polymer.

In another embodiment, the invention provides a polymer comprising made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with at least one bioactive agent; forming a liquid, bioactive agent-containing polymerizable mixture; applying the liquid, polymerizable mixture; initiating polymerization by an external stimulus; polymerizing for a period of time; thereby forming a drug-eluting polymer.

In another embodiment, the invention provides a polymer comprising made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with at least one bioactive agent; forming a liquid, bioactive agent-containing polymerizable mixture; applying the liquid, polymerizable mixture on tissue allograft(s); initiating polymerization by an external stimulus; polymerizing for a period of time; thereby forming a drug-eluting polymer.

In another embodiment, the invention provides a polymer comprising made by a process comprising the steps of: providing a liquid polymerizable mixture comprising a macromer that is a liquid at a temperature between about 10° C. and about 40° C., wherein the liquid polymerizable mixture is made by covalently linking a polyethylene glycol moiety of a molecular weight below 1000 g/mol to at least one biodegradable lactide moiety and covalently linking at least one cross-linkable acrylate moiety to the lactide moiety (sequentially or simultaneously, in the order desired); and at least one initiator; mixing with gentamicin; forming a liquid, bioactive agent-containing polymerizable mixture; applying the liquid, polymerizable mixture onto fixation devices including fracture plates and associated pins and screws; initiating polymerization by an external stimulus; polymerizing for a period of time; thereby forming a drug-eluting polymer.

By "drug eluting polymer", what is meant is a polymer which can release one or more bioactive agent(s) upon contact with an eluting environment. For example, a drug-eluting polymer formed on the surface of a femoral stem can start eluting the drug or drugs into the surrounding bone tissue after implantation of the stem into femoral canal during a total replacement surgery. In another example, a drug-eluting polymer formed on the surface of a fixation plate can start eluting drugs into the surrounding soft and hard tissue after fixation of plate by screws into fractured bone. In yet another example, a drug-eluting polymer formed on the non-articulating surfaces of a joint replacement, such as the side surfaces of a liner or the neck of the femur can start eluting drugs into the surrounding synovial fluid and soft tissues after implantation. In yet another example, a drug eluting polymer formed in the screw-hall openings of an acetabular shell or a tibial base plate can start eluting drugs into the surrounding space after implantation.

By "adhesive" (noun), what is meant is a chemical(s) or a mixture thereof to help adhere the drug eluting polymer to the surface or surfaces of a medical device. Such adhesive(s) can be chosen from the group of but are not limited to fibrin glue, or cyanoacrylate. In one embodiment, the adhesive(s) is applied between the surface of the medical device and the liquid, polymerizable mixture. The resultant drug-eluting polymer adheres to the surface of the medical device. The adhesive can be mixed with the liquid, polymerizable mixture before application to the surface(s) of the medical device. The adhesive can work as an adhesive in pre-mixed, or mixed state or can become an adhesive during or after polymerization of the liquid polymerizable mixture on the surface(s) of the medical device. In a preferred embodiment, the adhesive is cyanoacrylate, fibrin glue, and/or combinations thereof. In another preferred embodiment, the polymerizable mixture is polymerized and then adhered to the implant surface or to the implant reservoir by the use of an adhesive.

By "macromer", what is meant is a molecule with any molecular weight or a distribution of molecular weights comprising moieties such that a number of macromers can form new covalent bond(s) with each other and/or with other molecule(s). Macromers are made up of building blocks, the smallest of which is a monomer. Macromonomers are a subset of macromers where the building blocks are the same. In the present invention, macromers are built with different building blocks or moieties. In the prior art, the macromer is composed of biodegradable moiety and crosslinkable moieties (see US6,455,08B1). In particular, the prior art preferred embodiment is composed of 2-hydroxyethyl methacrylate (HEMA) as the cross-linkable moiety and caprolactone, and/or glycolide, and/or lactide as the biodegradable moieties (see US6,455,08B1). In present invention, the macromer is composed of a central or connecting moiety, one or more biodegradable moieties, and one or more cross-linkable moieties. In a preferred embodiment, the macromer is composed of two biodegradable moieties connected by a central connecting moiety and end capped with two or more cross-linkable moieties (FIG. 1). The connecting moiety can be multifunctional, star or dendritic for example. In another preferred embodiment, the macromer is composed of three or more biodegradable moieties, connected by tri- or more branched connecting moiety and end-capped with three or more crosslinkable moieties. For example, two poly(lactide) with average degree of polymerization of 2 are connected by polyethylene glycol with weight average molecular weight of 200 and then end-capped with two acrylate groups on each end. In another example, two poly(lactide) with average degree of polymerization of 4 are connected by polyethylene glycol with weight average molecular weight of 400 and then end-capped with two acrylate groups on each end. In another embodiment, the connecting moiety (optionally, a central connecting moiety) can be connected to at least one or more biodegradable moieties, which can then be connected to at least one or more cross-linkable moieties. The amount of readable moieties is not fixed and can be changed. The connecting moiety or the central connecting moiety can also be connected to at least one or more non-biodegradabale moieties By "connecting moiety" or optional "central connecting moiety" what is meant is a molecule or part of molecule that connects biodegradable moiety with biodegradable moiety, biodegradable moiety with cross-linkable moiety, and/or cross-linkable moiety with cross-linkable moiety. Such connecting moiety(ies) can be chosen from the group of but are not limited to polyethylene glycol, polyethylene oxide, polypropylene glycol, 1,6-hexanediol, 2,2,6,6-Tetrakis(hydroxymethyl)cyclohexanol, ethylene glycol, cyanuric acid. Such connecting moieties consist of a mixture of one or more types and consists of a mixture of different molecular weight distributions. In a preferred embodiment, the connecting moiety is liquid at room temperature. In one embodiment, the connecting moiety can be a mixture of polyethylene glycol and propylene glycol. The connecting moiety (for example, polyethylene glycol) can be of molecular weight of 200, 400, 600, 800, 1000 or less than 1000. In another embodiment, the connecting moiety can be a mixture of polyethylene glycol with average molecular weight of 200, 400, 600, 800, 1000 or less than 1000. In another embodiment, the connecting moiety has a random distribution(s) of weight average molecular weight polyethylene glycol. In the preferred embodiment, the connecting moiety can be polyethylene glycol with weight average molecular weight of 200 (PEG 200). In another preferred embodiment, the connecting moiety can be polyethylene glycol with weight average molecular weight of 400 (PEG 400).

By "biodegradable moiety", what is meant is a molecule or part of molecule that can be degraded (e.g. cleaved and/or destroyed and/or decomposed inside the body) and eliminated by the body. The cleaving, destroying, or decomposing can be through hydrolysis, enzymatic degradation, modification by the liver, excretion by the kidney(s) and/or combinations thereof. Modification by the liver means the changing of the degraded polymer by the liver. Such biodegradable moiety can be but not limited to poly(lactide) (PLA), poly(glycolide) (PGA), poly(epsilon-caprolactone) (PCA), poly(dioxane) (PDA), poly(trimethylene carbonate)

(PTMC), and combinations thereof. In one embodiment, the biodegradable moiety is polyglycolide. In another embodiment, the biodegradable moiety is polylactide-co-polyglycolide. In another embodiment, the biodegradable moiety is polytrimethylene carbonate-co-poly(epsilon-caprolactone). In a preferred embodiment, the biodegradable moiety is polylactide with length of 1-8 lactoyl groups. In another preferred embodiment, the biodegradable moiety is polyglycolide with length of 1-8 glycolyl groups. In another preferred embodiment, the biodegradable moiety is polycaprolactone with length of 1-8 epsilon-caprolactone groups. In certain preferred embodiments, the biodegradable moiety is a polylactide with 2-4 lactoyl groups.

By "cross-linkable moiety", what is meant is a molecule or part of a molecule that can form one or more new bond(s) (covalent and/or non-covalent) with another molecule, preferably a macromonomer to create a network of molecule(s) and/or macromonomers. Such cross-linkable moieties can comprise acrylate(s), methacrylate(s), thiols, carboxyls, hydroxyls, amino groups, isocyanates, azides, isothiocyanates, epoxides, and/or combinations thereof). In a preferred embodiment, the cross-linkable moiety comprises acrylate(s), methacrylate(s), or combinations thereof. In more preferred embodiment, the cross-linkable moiety comprises an acrylate group.

Polymerization of Macromers

In the present invention, the formulation used to create drug eluting polymer is composed of liquid, polymerizable mixture(s) of macromer(s) and additive(s). The liquid, polymerizable mixture(s) and additive(s) can be mixed to create another liquid polymerizable mixture. In a preferred embodiment, the liquid, polymerizable mixture, which is polymerized into a drug-eluting polymer, is composed of macromer(s), initiator(s), and inhibitor(s). In another preferred embodiment, the mixture is composed of macromer(s), and inhibitor(s). In another preferred embodiment, the mixture is composed of macromer(s), initiator(s), inhibitor(s), and bioactive agent(s).

By "additive", what is meant are components added into the liquid, polymerizable mixture other than the liquid macromer(s). These can be, for example, initiator(s) and/or bioactive agent(s) and/or inhibitor(s). They can also be additional molecules such as antioxidants or viscosity modifiers or emollients to change the solubility of different components in the liquid polymerizable mixture. In a preferred embodiment at least one additive is an initiator and a bioactive agent. In another preferred embodiment, the additive is a mixture of initiator(s), inhibitor(s), and bioactive agent(s). Additives can be added each into the liquid, polymerizable macromer(s) at a concentration between 0.0001 wt/vol % to 99 wt/vol %, preferably between 0.1 wt/vol % to 20 wt/vol %, more preferably between 0.1 wt/vol % to 5 wt/vol %, most preferably at 3 wt/vol %. The concentration of the initiator(s) in the liquid, polymerizable mixture can be 0.0001 wt/wt % to 10 wt/wt %, preferably between 0.01 and 2 wt/wt %, most preferably about 0.1 wt %. The concentration of the inhibitor(s) in the liquid, polymerizable mixture can be 0.0001 wt/vol % to 1 wt/vol %, preferably between 0.001 and 0.1 wt/vol %, most preferably 0.005 wt/vol %. The concentration of the bioactive agent or drug can be from 0.00001 to 99 wt/wt % or from 0.1 to 50 wt/wt %, preferably from 1 to 30 wt/wt %, more preferably from 5 to 30 wt/wt %.

By "initiator", what is meant molecule(s) that can initiate polymerization. Said initiator can be activated by light and/or heat and/or chemical means. Upon activation of the initiator, the initiator produces free radicals and/or cationic moieties and/or anionic moieties and interact with macromonomer to initiate polymerization. Said initiator can be activated by external stimuli such as light and/or radiation and/or heat and/or chemical means such as pH or ionic strength changes. Upon providing the external stimulus, the initiator can produce free radicals and/or cationic moieties and/or anionic moieties and interact with the macromer or macromer mixture to initiate its polymerization and/or cross-linking. Initiation can be done by shining ultraviolet light (260-400 nm), blue light (400 nm-500 nm), and/or other visible light (501-800 nm) for a certain period of time and certain radiance. Initiation can be done by heating. Initiating can be done by mixing two or more chemicals. Such initiators can be chosen from the group of but are not limited to benzophenone, 2,2-dimethoxy-2-phenylacetophenone, camphorquinone, ethyl 4-(dimethylamino) benzoate (EDMAB), 2.4.6-trimethylbenzoyldiphenylphosphine oxide, 1-Phenyl-1,2 propanedione, N,N-dimethyl-p-toluidine, Ciba Irgacure® 149, Ciba Irgacure® 184, Ciba Irgacure® 369, Ciba Irgacure® 500, Ciba Irgacure® 651, Ciba Irgacure® 784, Ciba Irgacure® 819, Ciba Irgacure® 907, Ciba Irgacure® 1700, Ciba Irgacure® 1800, Ciba Irgacure® 1850, Ciba Irgacure® 2959, Ciba Darocur® 1173, Ciba Darocur® 4265, Eosin, Rose Bengal, Benzil, Benzoin methyl ether, Isopropoxybenzoin, Benzoin phenyl ether, Benzoin isobutyl ether, Titanocene, benzoyl peroxide, N,N-dimethyl-p-toluidine, and combinations thereof. By light initiation is meant shining ultraviolet (260-400 nm), blue light (400 nm-500 nm), and/or visible light (501-800 nm) for a certain period of time and certain radiance to activate the initiator. By heat initiation is meant adding heat to activate the initiator. By chemical initiation is meant mixing two or more chemicals to activate the initiator. Such initiator can be but not limited to camphorquinone, ethyl 4-(dimethylamino) benzoate (EDMAB), 2.4.6-trimethylbenzoyldiphenylphosphine oxide, 1-Phenyl-1,2 propanedione, N,N-dimethyl-p-toluidine, and combinations thereof. In one embodiment, the initiator is heat sensitive and therefore adding heat to a mixture of macromonomer, initiator, and/or inhibitor, and/or bioactive agent initiates polymerization. In another embodiment, the initiator is light sensitive and therefore shining light of ultraviolet light (260-400 nm), blue light (400 nm-500 nm), and/or visible light (501-800 nm) to a mixture of macromonomer, initiator, and/or inhibitor, and/or bioactive agent initiates polymerization. In another embodiment, the initiator(s) is chemically reactive with each other and therefore mixing the macromonomer, initiator(s), and/or inhibitor, and/or bioactive agent initiates polymerization. Example of initiator that is heat sensitive is benzoyl peroxide. Example of initiator that is light sensitive is camphorquinone, ethyl 4-(dimethylamino) benzoate (EDMAB), 2.4.6-trimethylbenzoyldiphenylphosphine oxide, 1-Phenyl-1,2 propanedione. Example of initiator that is chemically reactive is N,N-dimethyl-p-toluidine, benzoyl peroxide. In a preferred embodiment, the initiator is light activated with blue light (400-500 nm). In more preferred embodiment, the initiator is camphorquinone, ethyl 4-(dimethylamino) benzoate (EDMAB), 2.4.6-trimethylbenzoyldiphenylphosphine oxide, and combinations thereof. In yet another preferred embodiment, the initiator is camphorquinone, ethyl 4-(dimethylamino) benzoate (EDMAB) and combinations thereof.

By "inhibitor" what is meant is a molecule or a mixture of molecules that can decrease the rate of polymerization or stop entirely the polymerization of polymerizable molecules. In this invention, the inhibitor is used to hinder the polymerization of the liquid, polymerizable mixture without deliberate stimulus to initiate polymerization. Inhibitors can be chosen from the group of but not limited to hydroquinone, mono methyl ether hydroquinone, 4-methoxyphenol, 4-tert-butylcatechol, or combinations thereof. In one embodiment the inhibitor is mixed with macromonomer to prevent unintentional polymerization. In another embodiment the inhibitor is mixed with macromonomer, initiator, inhibitor, and/or bioactive agent to prevent unintentional polymerization. In the preferred embodiment the inhibitor is hydroquinone. The inhibitor concentration in the liquid, polymerizable mixture can be 0.0001 wt % to 10 wt %, more preferably 0.01 wt % to 0.1 wt %, most preferably 0.05 wt %.

By "bioactive agent" what is meant is a molecule or a class of molecules that, when in contact with a living being can elicit reactions which result in a positive impact to the intended living being such as a human, or animal. By "in contact", what is meant is delivery methods of the bioactive agent, that is, bioactive agents can be administered by contact with the skin, by ingestion, by inhalation, by injection into soft tissue or directly into blood. Such positive impact may include reducing pain, reducing infection, reducing neoplastic cells, reducing inflammation, and combinations thereof. Such bioactive agent can be but not limited to antibiotics, anesthetics, antifibrinolyric, antineoplastic, and combinations thereof. Antibiotics can be chosen from the groups of aminoglycosides, beta-lactams, linear peptides, glycopeptides, dalbaheptides, lantibiotics, cyclic peptides, thiazolylpeptides, macrolactones, macrolides, difimycin, ansamycin, rifamycins, tetracylines, oxazolidinenones, lincosamides, pleuromutilins, quinolones, aminocoumarins. Examples of antibiotics are penicillin, imipenem, cefotaxime, ceftaroline, kanamycin, gentamycin, tobramycin, carbapenems, teicoplanin, dalbavancin, vancomycin, oritavancin, daptomycin, dalfopristin, amphomycin, colistins, ramoplanin, azithromycin, cethromycin, erythromycin, rifamycin, rifapentin, rifaximin, minocycline, tigecicline, linezolid, clindamycin, ciprofloxacin and rifampin. Examples of anesthetics are lidocaine, bupivacaine, ropivacaine, levobupivacaine, benzocaine, chloroprocaine, novocaine. Examples of antifibrinolyrics are tranexamic acid, aminocaproic acid. Examples of antineoplastics are doxorubicin, cisplatin, carboplatin, etoposide, ifosfamide, cyclophosphamide, methotrexate, vincristine. In preferred embodiments, the bioactive agent is an antibiotic or mixture of antibiotics. In a preferred embodiment, the bioactive agent is gentamicin, tobramycin, vancomycin, cefazolin, cephalexin, rifampin, ciprofloxacin, or combinations thereof.

By "polymerizable liquid" or "polymerizable liquid mixture", what is meant is at least one chemical substance in the liquid state at room temperature, or mixture of chemical substances in the liquid state at room temperature, which can become a solid or gel upon polymerization. In the liquid state, the substance or mixture can flow and/or change shape upon mechanical disturbance. The liquid mixture can be a liquid; that is, there can be gaseous or solid components dispersed in the liquid; as long as the mixture is able to flow and is homogeneous, it is termed a polymerizable liquid mixture. Similarly, all components can be dissolved in each other, thus the liquid could be a solution or a multi-component solution. The components of the mixture can have primary functions such as being a cross-linkable macromer, an initiator, or a cross-linking enhancer but can also aid in the solvation of other components. The liquid polymerizable mixture can also have non-polymerizable or non-reactable polymeric components, for example oligomers of polyethylene glycol.

Such a polymerizable liquid mixture can contain at least one macromonomer or macromer and at least one polymerization initiator and/or at least one inhibitor and/or at least one bioactive agent. In one embodiment a macromer is mixed with a bioactive agent and an initiator to create the polymerizable liquid mixture. Upon activation of the initiator(s) in the polymerizable liquid mixture is made by the appropriate external stimulus such as with light and/or heat and/or chemical means, polymerization occurs, resulting in a drug-eluting polymer.

By "polymerization", what is meant is the reaction of monomers or macromers with each other to form covalent bonds and a larger molecule or molecules, which are no longer able to readily react with each other. Said initiating can be through light and/or heat and/or chemical means. In one embodiment, the initiator is heat sensitive and therefore adding heat to a mixture of macromer, initiator, and/or inhibitor, and/or bioactive agent initiates polymerization. In another embodiment, the initiator(s) can undergo a spontaneous chemical reaction with one or more of the other additives or the macromer(s); therefore, mixing the macromer(s), initiator(s), and/or inhibitor(s), and/or bioactive agent(s) and/or other additives initiates polymerization. In a preferred embodiment, the initiator is light sensitive and therefore shining light on a liquid, polymerizable mixture; for example a mixture of macromer(s), initiator(s), and/or inhibitor(s), and/or bioactive agent(s), initiates polymerization. In an another preferred embodiment, at least one initiator is blue light sensitive (400-500 nm), the initiator comprises camphorquinone and/or ethyl 4-(dimethylamino) benzoate (EDMAB), and/or the inhibitor comprises of hydroquinone, the bioactive agent can be chosen from the group of antibiotics such as gentamicin, tobramycin, vancomycin, cefazolin, cephalexin, rifampin, ciprofloxacin, and/or combinations thereof, and the macromer is a triblock polylactide-co-polyethylene glycol-co-polylactide with acrylate groups at both ends.

By "degree of polymerization", what is meant is the number of building blocks or 'mer's comprising a macromer. Typically, in polymers, an average degree of polymerization is defined as there are many molecules as a result of the polymerization with differing numbers of building blocks.

Applying the liquid, polymerizable mixture to medical device and polymerization to form Drug-Eluting Polymer In the present invention, the liquid, polymerizable mixture can be applied to one or more surfaces of medical device. After application of the liquid, polymerizable mixture to the surfaces of medical device, the initiator in the polymerizable liquid can be activated to create a drug eluting polymer. The components of the liquid, polymerizable mixture can be pre-mixed in any combination before the time of application.

The components of the liquid, polymerizable mixture can be produced in a sterile environment, can be sterile-filtered at the end of the manufacturing process before packaging or sterilized in packaged form.

Figure 2:
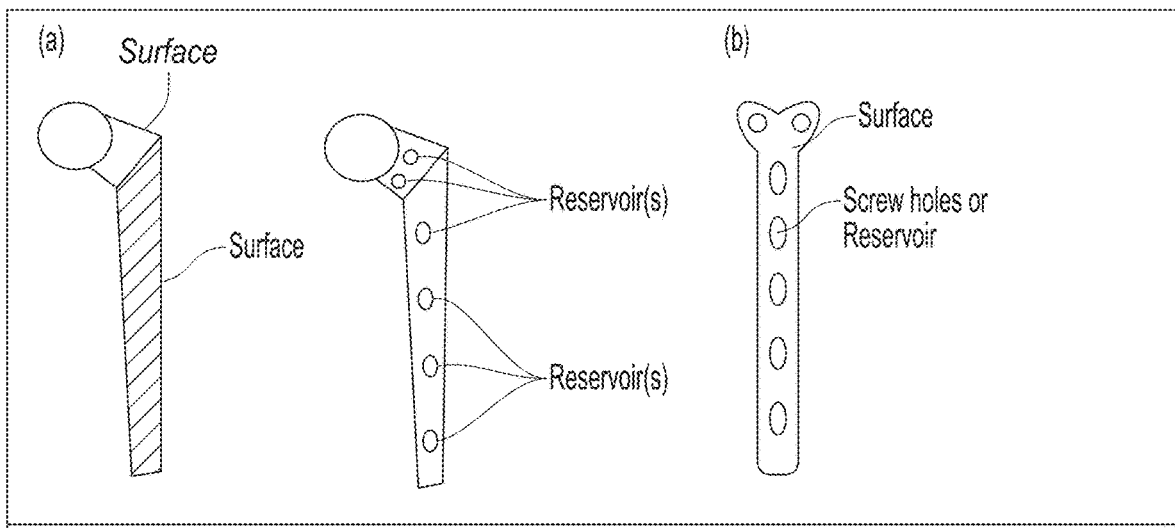
FIG. 2 is schematic depiction of an embodiment of the invention where the liquid polymerizable mixture is applied onto surface(s) of a femoral stem used in hip replacement surgery.

By "surface or surfaces of the medical device", what is meant is one or more areas on the outside surface(s) of the medical device where the liquid, polymerizable mixture can be applied (FIG. 2). Surface on the medical device is any area on the medical device exposed to the human, or animal, tissue and/or fluid upon use. In certain embodiments, the surface on the medical device is also modified by chemical and/or physical means. Surface modification can be done by but not limited to creating a physical well or a reservoir as a place where the drug eluting polymer can be added. In some embodiments, chemical modification of the surface of the medical device is used to allow for better adhesion of the drug eluting polymer (e.g. by grafting of acrylate, methacrylate, thiol, carboxyl, hydroxyl, amino groups, isocyanates, azides, isothiocyanates, epoxides, and/or a combination thereof on the surface of medical device). In some embodiments, texturing of the surface of the medical device (physically or through chemical etching) is used to provide a surface for the addition of the liquid polymerizable mixture. The surface of the medical implant where the liquid, polymerizable mixture is applied can be prepared in the factory or in the clinic, operating room, or in the doctor's office.

By "applying to the surface or surfaces of a medical device", what is meant is contacting one or more parts or all of the surfaces of a medical device with the liquid, polymerizable mixture is made by for example, filling pre-formed reservoirs on the surface(s) of the medical device with mixture, painting surface(s) of medical device with mixture, spraying surface of medical device by mixture and combinations thereof. The adhesion between the liquid, polymerizable mixture and the medical device surface can be enhanced by using an adhesive. Alternatively, the bond between the medical device surface and the drug-eluting polymer resulting from the polymerization of the liquid, polymerizable mixture on the surface of medical device can be enhanced by mechanical interfacing using design features on the medical device such as pores or locking features. This can also be enhanced by compressing or loading of the drug-eluting polymer onto the medical device surface. In one preferred embodiment, the polymerizable liquid is added as a layer on one or more reservoir(s) of a medical device and then polymerized. More preferably, the polymerizable liquid is added on the surface of a medical device and then polymerized. The liquid polymerizable mixture can be applied to the surface or surface(s) of implantable components such as tissue allograft(s). This application as well as further polymerization can be done before or after the allograft has been implanted. When the liquid polymerizable mixture is not applied to the surface or surfaces of a medical device, it can be applied directly at the site of treatment. Examples for the site of treatment can be the peri-prosthetic tissue around a fracture or a joint implant or degenerative disc(s) or a skin wound.

In one embodiment, the surface(s) include the backside or side walls of the tibial insert or tibial base plate used in total knee replacement. In another embodiment, the surface is along the femoral stem, on the rim of acetabular cup, backside of the acetabular cup as components of total hip replacement. In another embodiment, the surface is on the pacemaker pulse generator, inside or outside lumen of catheter.

In one embodiment, surface of the medical device can have reservoir(s). By "reservoir", what is meant is any surface feature that allows at least temporary containment of the liquid, polymerizable liquid (FIG. 2). In a preferred embodiment, the medical device has reservoir(s) that are previously machined and the liquid, polymerizable mixture is added into these reservoirs. In another embodiment, reservoir(s) can be formed on the medical device at the time of implantation; for instance in the operating room. In another embodiment, reservoir(s) are created in situ at the time of implantation by medical professionals such as but not limited to physician, nurses, physician assistant. In another preferred embodiment, the reservoirs are pre-formed or formed at the time of implantation on the backside of tibial inserts, sidewalls of tibial insert, rims of acetabular cups, backside of acetabular cups, femoral stems, tibial baseplates, knee femoral components, pacemakers, implantable cardioverter defibrillators, or catheters. In another embodiment, the reservoir is the space above the screw head inside a screw-hole of an acetabular shell or a tibial baseplate.

By "medical device", what is meant is an instrument, apparatus, implement, machine, implant or other similar and related article intended for use in the diagnosis, treatment, mitigation, cure, or prevention of disease in humans or other animals. An "implantable device" is a medical device intended to be implanted in contact with the human or other animal for a period of time. The primary function of the implantable medical device can be monitoring signals, delivering drugs or the replacement of tissues or the function of tissues among other functions. The implantable medical device can be permanent or can be removed after a period of time. A medical device can be made out of metal, polymer, ceramic or a combination thereof. A medical device can also contain organic tissue or modified organic tissue. Examples of implantable medical devices are acetabular shells, acetabular cups, femoral heads, modular or nonmodular femoral necks, tibial inserts, tibial baseplates, fixation pins, fracture plates, rods, screws, shoulder implants, pacemakers, ventricular assist devices, implantable cardioverter defibrillators. In an embodiment, the medical device is a urinary catheter, a central venous catheter, a femoral central venous catheter. In one embodiment, the medical device can be made of titanium alloy such as TiAl6V4, cobalt chrome alloy, poly ether ether ketone, ultrahigh molecular polyethylene, polyurethane, and combinations thereof. Fixation devices can be used collectively to indicate different components used in the fixation of a fracture, for example fracture plates, fixation pins and screws.

EXAMPLES

Example 1: Synthesis of PEG, Lactide, and Acrylate Based Liquid, Polymerizable Macromer DL-Lactide was recrystallized from ethyl acetate. Poly (ethylene glycol) (PEG) was dried under vacuum for 2 hr at 130° C. prior to use. Stannous octoate was used without further purification. In a flame dried round bottom flask, 4 grams of PEG 200 was added and then dried at 130° C. for 2 hr. Recrystallized DL-Lactide (5.8 gram, 0.04 mol) was added to the flask and the temperature was elevated to 150° C. After all the lactide melted, under nitrogen atmosphere, stannous octoate (60 mg, 0.1480 mol) was added to the solution. Reaction was allowed to proceed for 6 hr and then connected to vacuum to remove unreacted lactide. After an additional hour, the solution was cooled to room temperature. If necessary, additional purification steps were conducted where the resulting product was dissolved in dichloromethane and precipitated in hexane, filtered, and then dried. The product of this reaction is referred to as 21LP2.

21LP2 synthesized above (15.5 gram) was dissolved in anhydrous dichloromethane to create a final concentration of 10 mg/ml. Resulting solution was then cooled to 0° C. using an ice bath. Under nitrogen atmosphere, 11.15 ml (0.08 mol) of trimethylamine was added to the solution, followed by dropwise addition of 6.5 ml (0.08 mol) acryloyl chloride. Reaction was stirred for 24 hr and the solid trimethylamine hydrochloride was separated by filtration. The resulting macromer was purified by repeated dissolution in dichloromethane and re-precipitation in hexane. In this instance, the central, connecting moiety was PEG, the biodegradable moiety connected to the central moiety was polylactide and the cross-linkable moiety was acrylate. Table 1 lists some other macromers that were synthesized using this method.

TABLE 1

The composition and appearance of polymerizable macromers made of PEG as central moiety, polylactide as biodegradable moiety and acrylate as cross-linkable moiety.

| Polymer Name | Mol Wt % of PEG Chain (daltons) | Lactide to PEG mol ratio | Appearance at 25° C. |
|---|---|---|---|
| 21LP2 Diac | PEG 200 | 2:1 | Viscous liquid |
| 41LP2 Diac | PEG 200 | 4:1 | Viscous liquid |
| 61LP2 Diac | PEG 200 | 6:1 | Viscous liquid |
| 21LP4 Diac | PEG 400 | 2:1 | Viscous liquid |
| 41LP4 Diac | PEG 400 | 4:1 | Viscous liquid |
| 61LP4 Diac | PEG 400 | 6:1 | Viscous liquid |
| 21LP6 Diac | PEG 600 | 2:1 | Viscous liquid |
| 41LP6 Diac | PEG 600 | 4:1 | Viscous liquid |
| 61LP6 Diac | PEG 600 | 6:1 | Viscous liquid |

Similar procedure was used to synthesize macromers with glycolide (Table 2) and ε-Caprolactone in lieu of DL-Lactide (Table 3).

TABLE 2

The composition and appearance of polymerizable macromers made of PEG as central moiety, polyglycolide as biodegradable moiety and acrylate as cross-linkable moiety.

| Polymer Name | Mol Wt % of PEG Chain (daltons) | Glycolide to PEG mol ratio | Appearance at 25° C. |
|---|---|---|---|
| 21GP2 Diac | PEG 200 | 2:1 | Viscous liquid |
| 41GP2 Diac | PEG 200 | 4:1 | Wax |
| 21GP4 Diac | PEG 400 | 2:1 | Viscous liquid |
| 41GP4 Diac | PEG 400 | 4:1 | Wax |
| 21GP6 Diac | PEG 600 | 2:1 | Viscous liquid |
| 41GP6 Diac | PEG 600 | 4:1 | Wax |

TABLE 3

The composition and appearance of polymerizable macromers made of PEG as central moiety, polycaprolactone as biodegradable moiety and acrylate as cross-linkable moiety.

| Polymer Name | Mol Wt % of PEG Chain (daltons) | Caprolactone to PEG mol ratio | Appearance at 25° C. |
|---|---|---|---|
| 21CP2 Diac | PEG 200 | 2:1 | Viscous liquid |

Example 2: Spectral Characterization of Lactide Based Macromers

Figure 3:
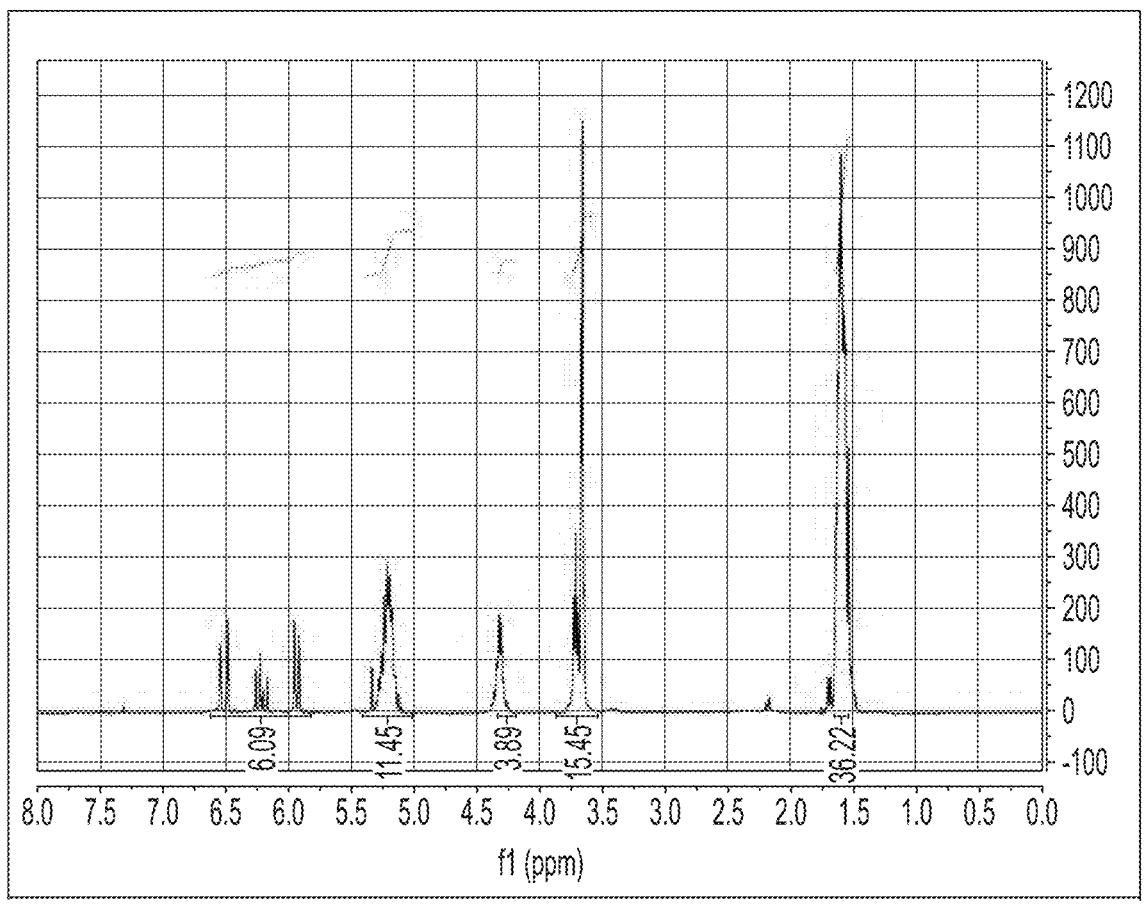
FIG. 3 is $^1$H NMR for a liquid, polymerizable macromer made of PEG200 as the central, connecting moiety, DL-lactide as the biodegradable moiety and acrylate as the cross-linkable moiety with a molar ratio of 6:1 lactide to PEG units (61LP2 diac).

Nuclear magnetic resonance (NMR) and Fourier Transform Infrared (FTIR) spectroscopy was used to characterize the structure and purity of the macromers containing lactide prepared as described in Example 1. To prepare the $^1$H NMR sample, 10 mg of the macromer was dissolved in deuterated chloroform (CDCl$_3$). $^1$H NMR was obtained at 300 MHz. $^1$H NMR for 61LP2 disc is provided in FIG. 3.

Sample for FTIR spectroscopy was prepared by dissolving 10 mg of the macromer in chloroform and then added dropwise onto an infrared transparent-NaCl plate. Chloroform was allowed to evaporate for 30 minutes at room temperature before FTIR spectra was measured. FTIR spectra of 61LP2 diac: 1110 cm$^{-1}$ (C—O bond of PEG), 1755 cm$^{-1}$ (C=O of lactide), 1590 cm$^{-1}$ (C=C of acrylate groups).

These results showed that the designed stoichiometry was achieved for the liquid, biodegadable, polymerizable macromers.

Figure 4:
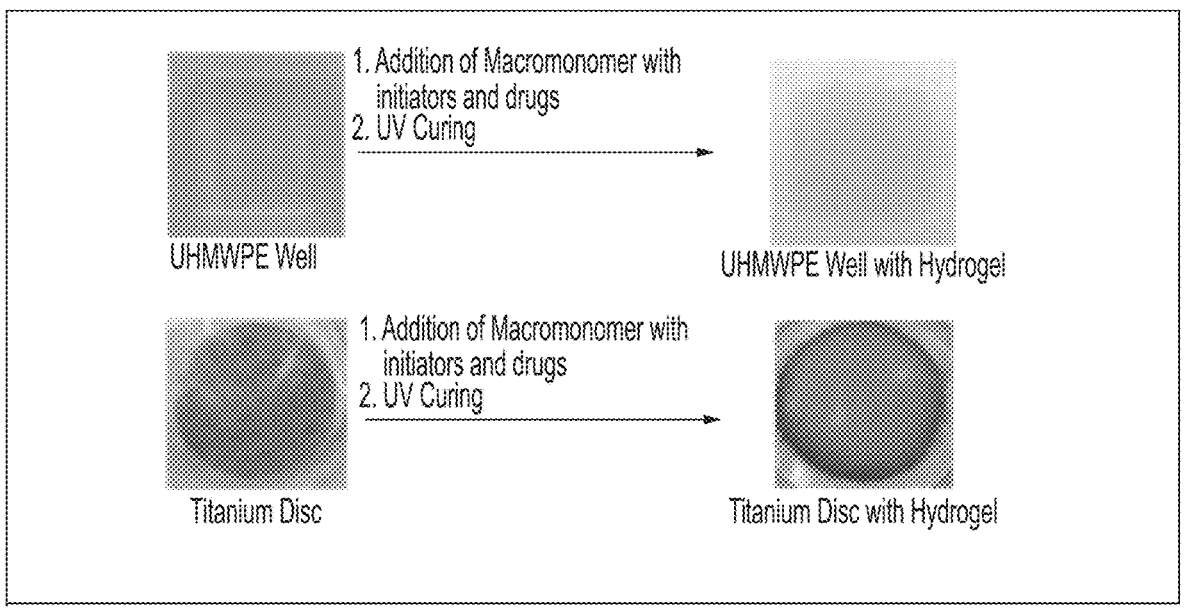
FIG. 4 schematically depicts photopolymerization of a liquid, polymerizable mixture containing gentamicin on UHMWPE and titanium surfaces.

Example 3: Synthesis of Gentamycin-Eluting Hydrogel from Liquid, Polymerizable Macromer A solution containing 0.0084 gram of camphorquinone (1 ml) and 0.0034 gram of ethyl-4-dimethylamino benzoate (EDMAB) in dichloromethane was added 1 gram of 21LP2 Diac. After a homogeneous solution was obtained, 0.1 gram of gentamycin sulfate was added to create a suspension. Dichloromethane was then removed under vacuum. The resulting viscous suspension was then added to at 1 cm×1 cm×0.7 mm well made on the surface of a sheet of Ultra High Molecular Weight Polyethylene (UHMWPE). The solution was then photopolymerized using 700 mW/cm$^2$ UV-Blue light from UV Curing Spot Lamp (Dymax Blue Wave 200) for 30 s. Resulting hydrogel is showed in FIG. 4. A control hydrogel without the presence of drug was also prepared.

To synthesize the photopolymerized hydrogel on a titanium surface, similar procedure was conducted as mentioned above with titanium is used instead of UHMWPE.

These results showed the feasibility of photopolymerizing the synthesized liquid, polymerizable macromer(s) in the presence of a bioactive agent and on surfaces representative of medical device surfaces.

Example 4: Accelerated In Vitro Biodegradation

Figure 5:
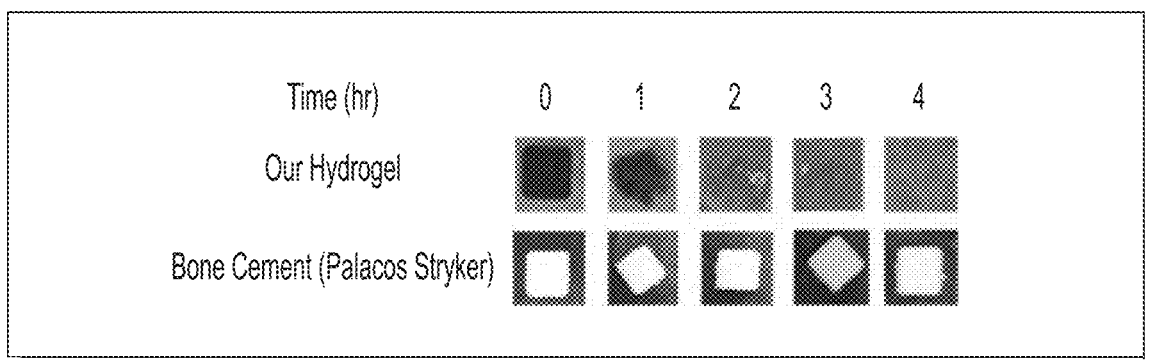
FIG. 5 depicts the biodegradation of a representative biodegradable, drug-eluting hydrogel made according to this invention compared to bone cement.

A LP2Diac macromer was photopolymerized in the presence of gentamicin as described in Example 3 in UHMWPE wells (1 cm×1 cm×0.5 mm). The resulting hydrogels were separated from the UHMWPE surface and immersed in 1M NaOH (10 ml) at room temperature. Time to completely dissolve some of the gel was shown in Table 4. Representative progression of hydrolytic degradation was shown in FIG. 5.

TABLE 4

Biodegradation time for different formulations of macromers

| Macromer | Time to Completely Dissolve in 1M NaOH |
|---|---|
| 21LP2 Diac | 4 hr |
| 21LP4 Diac | 2 hr |
| 21LP6 Diac | 30 min |
| Bone Cement (Palacos Zimmer) | is not degradable |

These results showed that it was feasible to manipulate biodegradation time for the drug-eluting hydrogels by changing the formulation of the liquid, polymerizable macromer, from which they were polymerized.

Example 5: In Vitro Biodegradation Under Physiologically Relevant Condition

Figure 6:
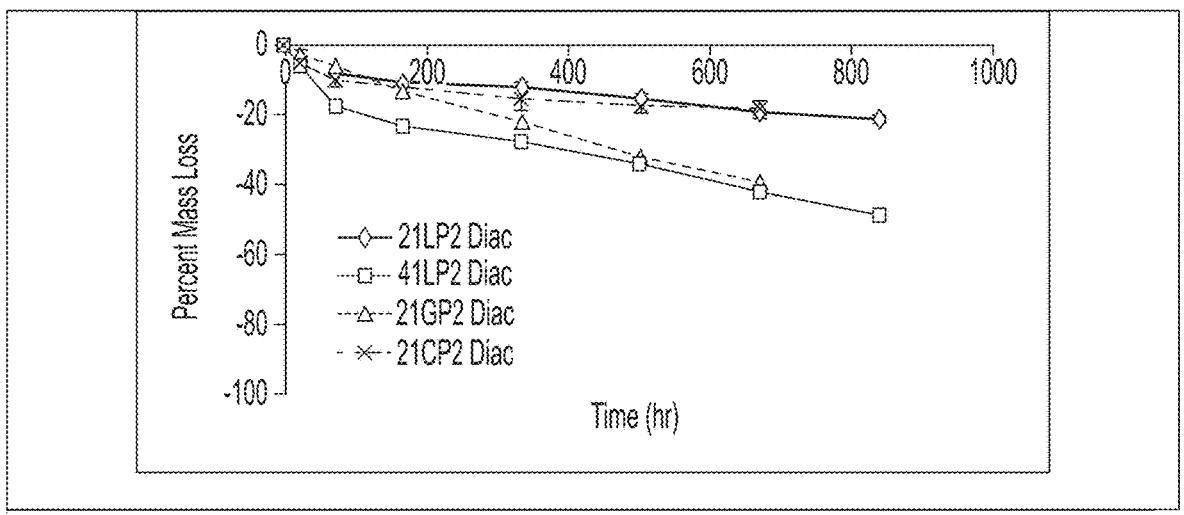
FIG. 6 is a graph depicting the degradation (weight loss) profiles as a function of time for hydrogels polymerized using different formulations of liquid macromer.

To measure the in vitro hydrolytic degradation, hydrogels were placed in normal saline (0.9% NaCl), pH 7.4 at 37° C. After predetermined time point is achieved, hydrogels were dried at 70° C. for 6 hr under vacuum. Samples are then weighed to determine mass loss in the gel. Degradation profile of some of the gel was shown in FIG. 6.

In general, the degradation was in two phases: a faster linear phase in the first week was followed by a second, slower linear phase. Among the 2:1 ratio of (lactide (21LP2 Diac), glycolide (21GP2 Diac), or ε-caprolactone (21CP2 Diac)) to PEG 200, 21GP2 Diac had the fastest degradation rate, followed by 21CP2 Diac, and then 21LP2 Diac. Increasing mole ratio of Lactide to PEG 200 from 2:1 to 4:1 increased the degradation rate.

These results showed that it was feasible to manipulate biodegradation time for the drug-eluting hydrogels by changing the formulation of the liquid, polymerizable macromer, from which they were polymerized.

Figure 7:
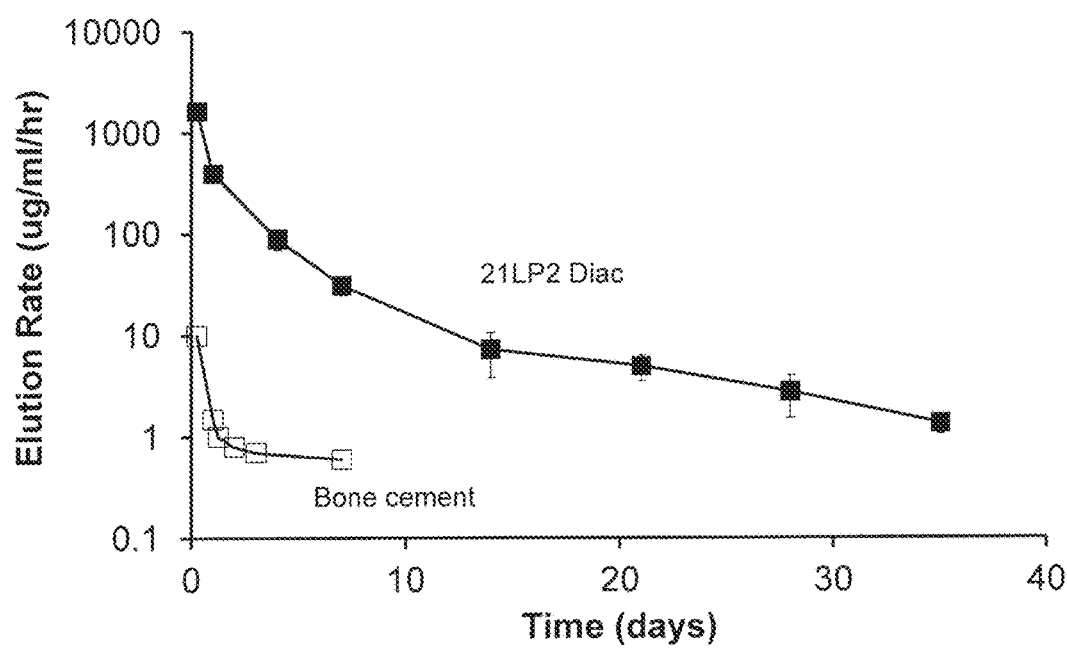
FIG. 7 is a graph depicting the concentration of gentamicin eluted into PBS at physiological conditions from a drug-eluting polymer prepared according to this invention compared to that from bone cement.

Example 6: In Vitro Elution of Gentamycin Under Physiologically Relevant Conditions Gentamycin eluted from a drug-eluting hydrogel (21LP2 Diac) polymerized as described in Example 3 was measured at different time points. 1 cm×1 cm×0.7 mm gentamycin was immersed in 1 ml phosphate buffered saline (PBS; pH=7.4), at 37° C. When predetermined elution time was reached, the gentamycin concentration in the solution was measured using tandem liquid chromatography-mass spectroscopy (LC-MS). All samples were then washed with PBS and then immersed in a fresh 1 ml phosphate buffered saline. Commercially available gentamycin eluting bone cement (Palacos, Zimmer) with the same dimension as the hydrogel samples was used as comparison (FIG. 7).

At all-time points the 21LP2 Diac eluted higher concentration of gentamycin than the bone cement control. These results showed that a drug-eluting polymer with a more effective antibiotic elution concentration profile than the predicate clinical device could be obtained by the methods described herein.

Example 7: Biocompatibility and In Vivo Degradation Using a Murine Subcutaneous Model Biocompatibility of hydrogel made of LP2Diac macromer was evaluated. To evaluate the biocompatibility and the in vivo degradation of the hydrogel, four different type of materials were implanted in the dorsal subcutaneous pockets of BL6/C57 fully immune-competent mice; The first group (n=3) received 5 mm×5 mm×0.7 mm polymerized bone cement (Palacos, Zimmer). The second group (n=3) received injection of 250 uL of the mixture of 21LP2 Diac, 0.0021 gram of camphorquinone and 0.0009 gram of ethyl-4-dimethylamino benzoate (EDMAB). The second group (n=3) received an injection of 250 uL of the mixture of PEG 600, 0.0021 gram of camphorquinone and 0.0009 gram of ethyl-4-dimethylamino benzoate (EDMAB). The last group received 5 mm×5 mm×0.7 mm polymerized hydrogel made from the macromer 21LP2 Diac in the presence of the above additives photopolymerized as described in Example 3 on a UHMWPE surface. Mice were euthanized after four weeks. Dorsal skin of all the mice were dissected, area surrounding the implants were isolated and fixed in 10% neutral buffered formalin, blocked in paraffin, sectioned, and stained using hematoxyline and eosin.

No gross adverse tissue reaction was evident on any of the mice (FIG. 12). All bone cement implants retained their shape and no significant change in dimension was observed. All polymerized hydrogels underwent significant degradation, and none retained its original shape. No trace of 21LP2 DIac or PEG 600 or the initiators was found in either of the injection groups, indicating that both the mixtures were absorbed and removed by the body. These results showed that neither the drug-eluting polymer nor its degradation products resulted in a chronic inflammation or unexpected adverse effects in the mouse subcutaneous contact model.

Example 8: Bactericidal Activity of Gentamycin-Eluting Hydrogel Using a Murine Subcutaneous Model Efficacy of a gentamycin-eluting polymer polymerized on a titanium disc was tested against bioluminescent *S. aureus* (Xen 29) in the dorsal subcutaneous pockets of BL6/C57 fully immune-competent mice. Six mice were randomly divided into two groups: Control group and hydrogel group (n=3 each). Mice in the control group received a sterile titanium disc (Diameter=9 mm, thickness=3 mm). Mice in the hydrogel group received a sterile titanium disc with gentamycin-containing polymer photopolymerized on its surface. The liquid, polymerizable mixture contained 0.1 gram of gentamycin sulfate, 0.0084 gram camphorquinone, and 0.0034 EDMAB, and 1 ml of LP2Diac macromer was photopolymerized with 380-500 nm wavelength, 700 mW/cm$^2$ for 30 s time. After all implants have been placed in the dorsal subcutaneous pocket of the mice, each mouse received 5×10$^7$ cfu of Xen 29 in 20 uL saline around the implant. Bioluminescence was measured before and after the bacterial injection, also at 24 hr, 48 hr, 96 hr, and 1 week. To test the bactericidal activity of the hydrogel after 1 week of implantation, at 1 week, mice in the hydrogel group received injection of 5×10$^7$ cfu of Xen 29 in 20 uL saline. Bioluminescence was then measured again right after injection, also at 24 hr, 48 hr, 96 hr, and 1 week. All control mice are euthanized at 1 week.

Figure 8:
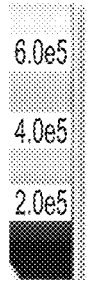
FIGS. 8 (a) and 8 (b).

Bioluminescence in the control and treated groups is shown in FIG. 8a, and the bioluminescence quantification is shown in FIG. 8b. There was no statistical difference in bioluminescence between control and hydrogel group right after bacterial injection, indicating that both arms of the study received relatively the same amount of live bacteria. In the control group bioluminescence increased after 24 hr and kept relatively constant until one week. In the hydrogel group, no bioluminescence was observed after 24 hr. In the second bacterial injection of the hydrogel group, no bioluminescence was observed after 4 days.

These results suggested that despite repeated stressing with bacteria, the drug-eluting polymer could eradicate the bacteria around a simulated medical device in the murine subcutaneous model.

Example 9: In Vitro Biocompatibility of Hydrogel as Compared to PMMA Bone Cement In vitro biocompatibility of hydrogel made of LP2Diac macromer and PMMA bone cement was evaluated. To evaluate the biocompatibility, murine macrophage (RAW 264.7) was cultured for 24 hour on the surface of PMMA bone cement and polymerized hydrogel made from LP2Diac in the presence of the above additives photopolymerized as described in Example 3 on a UHMWPE surface (FIG. 9). Number of live macrophages on the surface of hydrogel of PMMA bone cement was imaged using fluorescence live-dead stain and quantified using CCK-8 assay.

More live bacteria was observed through fluorescence microscope on the hydrogel surface than PMMA bone cement. CCK-8 assay also showed higher amount of live macrophages on the hydrogel surface than PMMA bone cement. These results indicated that the hydrogel was at least as biocompatible as clinically used PMMA bone cement.

Example 10: Antibacterial Activity of Hydrogel Combined with Blue Light

To establish the ability of hydrogel without additional antibiotics to eradicate bacteria, liquid culture of bioluminescent S. aureus was exposed to one of the four treatments: (1) Nothing (control), (2) 380-500 nm wavelength, 700 mW/cm$^2$ for 30 s (blue light), (3) hydrogel only (hydrogel, comprised of liquid, polymerizable mixture contained 0.0084 gram camphorquinone, and 0.0034 EDMAB, and 1 ml of LP2Diac macromer), and (4) The liquid, polymerizable mixture contained, 0.0084 gram camphorquinone, and 0.0034 EDMAB, and 1 ml of LP2Diac macromere, which was photopolymerized with 380-500 nm wavelength, 700 mW/cm$^2$ for 30 s time after added to the bacterial culture (hydrogel+blue light) (FIG. 10). Presence of live bacteria was detected using bioluminescent imaging (FIG. 10a) and fluorescence live-dead microscopy (FIG. 10b).

Complete eradication of bacteria and absence of formation of biofilm was observed in hydrogel+blue light. Small amount of live bacteria can be observed in hydrogel only or blue light only, while treatment with nothing showed mostly live bacteria (FIG. 10).

Example 11: Biofilm Formation Prevention by Hydrogel Covered Titanium Surface To establish the ability of hydrogel in preventing biofilm formation, titanium discs covered with hydrogel made from polymerized liquid polymerizable mixture was exposed for 24-hour to bioluminescent S. aureus. The liquid, polymerizable mixture contained, 0.0084 gram camphorquinone, and 0.0034 EDMAB, and 1 ml of LP2Diac macromer was photopolymerized with 380-500 nm wavelength, 700 mW/cm$^2$ for 30 s time.

Complete eradication of bacteria and absence of formation of biofilm was observed in the titanium disc coated with hydrogel and receiving additional in situ blue light treatment (FIG. 11).

Example 12: In Situ Spraying and Polymerization of Gentamicin Eluting Hydrogel on the Titanium Surface Feasibility to spray gentamicin containing polymerizable mixture of 0.0084 gram camphorquinone, and 0.0034 EDMAB, and 1 ml of LP2Diac on medical surface and subsequent polymerization with light was demonstrated (FIG. 13). The polymerizable mixture with ingredients mentioned above came in a sterile vial. Gentamicin powder was then added into the polymerizable mixture and sprayed onto the titanium surface. The polymerizable mixture containing gentamicin was subsequently photopolymerized with 380-500 nm wavelength, 700 mW/cm$^2$ for 30 s time to yield hydrogel thickness of 1-5 mm.

Example 13: Longer Term Bactericidal Activity of Gentamycin-Eluting Hydrogel Using a Murine Subcutaneous Model Longer term efficacy of a gentamycin-eluting polymer polymerized on a titanium disc than example 8 was tested against bioluminescent S. aureus (Xen 29) in the dorsal subcutaneous pockets of BL6/C57 fully immune-competent mice (FIG. 14). Fifty mice were randomly divided into two groups: Control group and hydrogel group (n=25 each). Mice in the control group received a sterile titanium disc (Diameter=9 mm, thickness=3 mm). Mice in the hydrogel group received a sterile titanium disc with gentamycin-containing polymer photopolymerized on its surface. The liquid, polymerizable mixture contained 0.1 gram of gentamycin sulfate, 0.0084 gram camphorquinone, and 0.0034 EDMAB, and 1 ml of LP2Diac macromer was photopolymerized with 380-500 nm wavelength, 700 mW/cm$^2$ for 30 s time.

After all implants have been placed in the dorsal subcutaneous pocket of the mice, the mice from the control and hydrogel groups were further randomly divided into five groups for bacterial injections time: (1) Received bacteria injection immediately after implantation (n=5 control, n=5 hydrogel), (2) Received bacteria injection one week after implantation (n=5 control, n=5 hydrogel), (3) Received bacteria injection two weeks after implantation (n=5 control, n=5 hydrogel), (4) Received bacteria injection three weeks after implantation (n=5 control, n=5 hydrogel), (5) Received bacteria injection four weeks after implantation (n=5 control, n=5 hydrogel). The bacteria injection consisted of 5×10$^7$ cfu of Xen 29 in 20 uL saline around the implant. Bioluminescence was measured immediately after the bacterial injection, also at 24 hr, 48 hr, 96 hr, and 1 week.

Bioluminescence in the control and treated groups is shown in FIG. 14a, and the bioluminescence quantification is shown in FIG. 14b. There was no statistical difference in bioluminescence between control and hydrogel group right after bacterial injection for all bacterial injections time, indicating that both arms of the study received relatively the same amount of live bacteria. Bacteria were eradicated in all bacterial injections time groups in the hydrogel arm of the study. The immune system alone did not successfully eradicate bacteria in all injection time groups, as shown by presence of bacteria one week after injections in the control groups.

Example 14: In Vivo Antibacterial Activity of Gentamicin Eluting Hydrogel in Murine Midshaft Fracture Model Efficacy of a gentamycin-eluting polymer polymerized on a titanium fracture plate was tested against bioluminescent S. aureus (Xen 29) in the setting of midshaft femoral fracture in rat (FIG. 15). After incision and exposure of the lateral femur, a sterile titanium plate (Length=25 mm, width=5 mm, thickness=3 mm) was implanted on the femur (FIG. 15). Wire saw was then used to create midshaft fracture in the middle of the femur. The rats (n=6) were then randomly divided into two groups: Control group and hydrogel group (n=3 each). Rats in the control group received spray of saline on the surface of the titanium plate. Rats in the hydrogel group received spray of gentamycin-containing photopolymerizable liquid hydrogel on its surface. The liquid, polymerizable mixture contained 0.1 gram of gentamycin sulfate, 0.0084 gram camphorquinone, and 0.0034 EDMAB, and 1 ml of LP2Diac macromer was photopolymerized with 380-500 nm wavelength, 700 mW/cm$^2$ for 30 s time.

After implantation, each mouse received 5×10$^7$ cfu of Xen 29 in 20 uL saline around the implant. Bioluminescence was measured before and after the bacterial injection, also at 24 hr, 48 hr, 96 hr, and 1 week (FIG. 16).

Bioluminescence in the control and treated groups is shown in FIG. 16. There was no statistical difference in bioluminescence between control and hydrogel group right after bacterial injection, indicating that both arms of the study received relatively the same amount of live bacteria. In the control group bioluminescence increased after 24 hr and kept relatively constant until one week. In the hydrogel group, no bioluminescence was observed after 24 hr.

Figure 17:
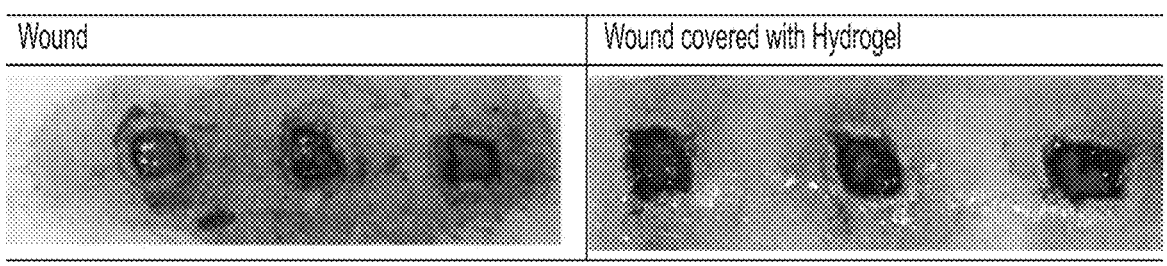
FIGS. 17 (a), 17 (b) and 17 (c) depict application of hydrogel as antibacterial wound dressing and cover.
Figure 17:
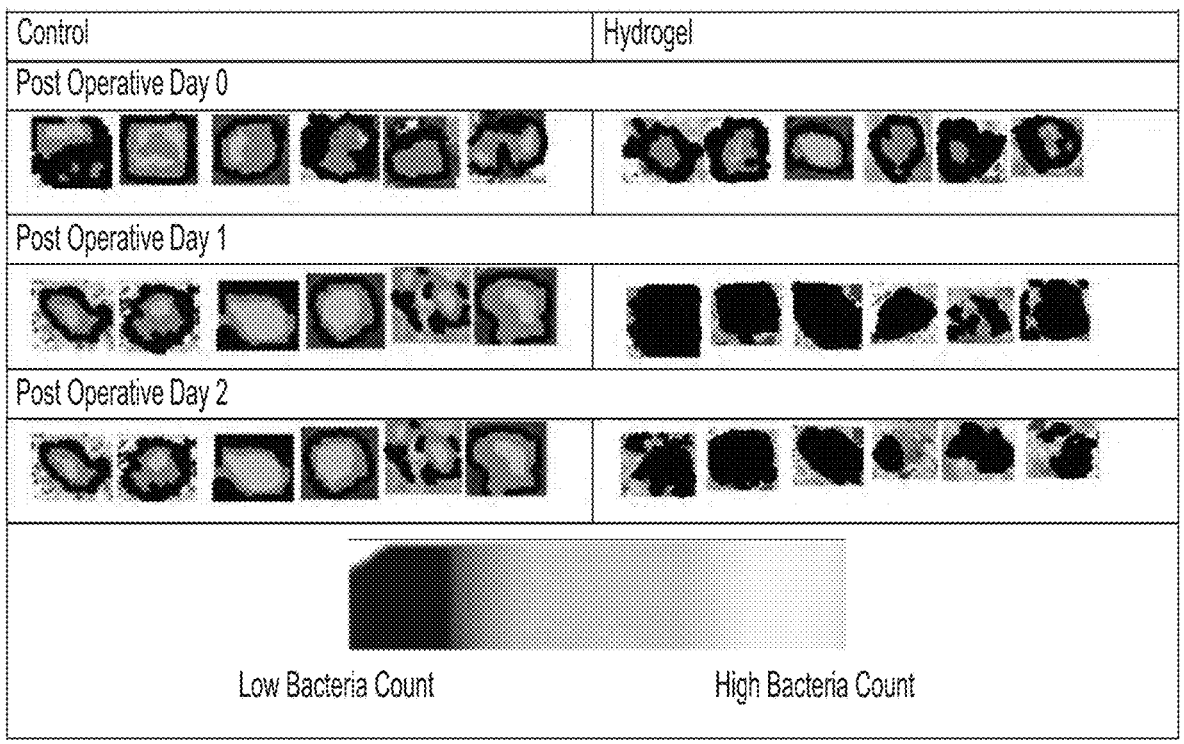

Example 15: In Vivo Antibacterial Activity of Non-Antibiotic Eluting Hydrogel in Murine Wound Model Efficacy of a hydrogel+blue light against bioluminescent S. aureus (Xen 29) in the setting cutaneous wound was demonstrated (FIG. 17). After incision of the full thickness of the skin on the dorsum of rat (FIG. 17), $5\times10^7$ cfu of Xen 29 in 20 uL saline was added to the wound. The rats (n=6) were then randomly divided into two groups: Control group and hydrogel group (n=3 each). Rats in the control group received Tegaderm® (3M) for covering of the wound surface. Rats in the hydrogel group received spray of photopolymerizable liquid hydrogel to cover the wound. The photopolymerizable liquid hydrogel contained 0.0084 gram camphorquinone, and 0.0034 EDMAB, and 1 ml of LP2Diac macromer was photopolymerized with 380-500 nm wavelength, 700 mW/cm$^2$ for 30 s time.

Bioluminescence was measured before and after the bacterial injection, also at 24 hr, 48 hr, and 120 hr (FIG. 17).

Bioluminescence in the control and treated groups is shown in FIG. 17. There was no statistical difference in bioluminescence between control and hydrogel group right after bacterial injection, indicating that both arms of the study received relatively the same amount of live bacteria. In the control group bioluminescence increased after 24 hr and kept increasing at 48 hr. In the hydrogel group, bioluminescence was reduced after 24 hr and was relatively constant to 120 hr. No difference in bioluminescence was observed between control and hydrogel group at 120 hr.

What is claimed is:

1. A method of making a medical device comprising a drug-eluting biodegradable polymer, wherein the method comprises the steps of:
    providing a liquid polymerizable mixture comprising at least a macromer that is a liquid at a temperature between about 10° C. and about 40° ° C. without addition of a solvent, wherein the macromer comprises a first and a second cross-linkable moieties, a first and a second biodegradable moieties, and polyethylene glycol (PEG) 200 as a central moiety, wherein the macromer is comprised of one selected from the group consisting of the covalent bonding of:
    (A) the first cross-linkable moiety, the first biodegradable moiety, PEG 200 as a connecting moiety, the second biodegradable moiety, and the second cross-linkable moiety,
    (B) the first cross-linkable moiety, the first biodegradable moiety, PEG 200 as a connecting moiety, the second cross-linkable moiety, and the second biodegradable moiety,
    (C) the first biodegradable moiety, the first cross-linkable moiety, PEG 200 as a connecting moiety, the second cross-linkable moiety, and the second biodegradable moiety, and
    (D) the first biodegradable moiety, the second cross-linkable moiety, PEG 200 as a connecting moiety, the second biodegradable moiety, and the second cross-linkable moiety;
    wherein the first and the second cross-linkable moieties are the same or different;
    wherein the first and the second biodegradable moieties are the same or different;
    mixing with at least one bioactive agent without addition of a solvent, thereby forming a liquid, bioactive agent-containing polymerizable mixture;
    applying the liquid polymerizable mixture without addition of a solvent onto at least one surface of an implant;
    initiating polymerization by an external stimulus without addition of a solvent;
    polymerizing for a period of time; thereby forming the medical device comprising the biodegradable drug-eluting polymer.

2. A method of making a medical device comprising a drug-eluting polymer, wherein the method comprises the steps of:
    providing a liquid polymerizable mixture comprising at least a macromer that is a liquid at a temperature between about 10° C. and about 40° ° C. without addition of a solvent, wherein the macromer comprises a first and a second cross-linkable moieties, a first and a second biodegradable moieties, polyethylene glycol (PEG) 200 as a central moiety, wherein the macromer is comprised of one selected from the group consisting of the covalent bonding of:
    (A) the first cross-linkable moiety, the first biodegradable moiety, PEG 200 as a connecting moiety, the second biodegradable moiety, and the second cross-linkable moiety,
    (B) the first cross-linkable moiety, the first biodegradable moiety, PEG 200 as a connecting moiety, the second cross-linkable moiety, and the second biodegradable moiety,
    (C) the first biodegradable moiety, the first cross-linkable moiety, PEG 200 as a connecting moiety, the second cross-linkable moiety, and the second biodegradable moiety, and
    (D) the first biodegradable moiety, the first cross-linkable moiety, PEG 200 as a connecting moiety, the second biodegradable moiety, and the second cross-linkable moiety;
    wherein the first and the second cross-linkable moieties are the same or different;
    wherein the first and the second biodegradable moieties are the same or different;
    mixing with an anesthetic agent without addition of a solvent, thereby forming a liquid, bioactive agent-containing polymerizable mixture;
    applying the liquid polymerizable mixture onto at least one surface of an implant;
    initiating polymerization by an external stimulus without addition of a solvent;
    polymerizing for a period of time; thereby forming the medical device comprising the drug-eluting biodegradable polymer for drug elution.

3. The method according to claim 1, wherein the medical device is selected from the group consisting of a fracture plate, an internal fixation (fracture) plate, an acetabular shell, an acetabular cup or femoral stem of a total hip replacement implant, a femoral or tibial component or patellar component of a total knee replacement implant, any component of a total hip replacement, any component of a hip resurfacing implant, femoral heads, modular or nonmodular femoral necks, tibial inserts, tibial baseplates, fixation pins, rods, screws, and shoulder implants.

4. The method according to claim 1, wherein the first cross-linkable moiety and the second cross-linkable moiety are selected from the group consisting of acrylates, methacrylates, thiols, carboxyls, hydroxyls, amino groups, isocyanates, azides, isothiocyanates, epoxides, and a combination thereof.

5. The method according to claim 1, wherein the first biodegradable moiety and the second biodegradable moiety are selected from the group consisting of poly(lactide) (PLA), poly(glycolide) (PGA), poly(epsilon-caprolactone) (PCA), poly(dioxane) (PDA), poly(trimethylene carbonate) (PTMC), and any combination thereof.

6. The method according to claim 1, wherein the first connecting moiety and the second connecting moiety are selected from the group consisting of polyethylene glycol, polypropylene glycol, 1,6-hexanediol, 2,2,6,6-Tetrakis(hydroxymethyl)cyclohexanol, ethylene glycol, and cyanuric acid.

7. The method according to claim 1, wherein the external stimulus to initiate polymerization of the liquid polymerizable mixture is carried out by
at least one selected from the group consisting of:
(i) heating with a power of 700 mW/cm2 to 1400 mW/cm2, and
(ii) changing pH.

8. The method according to claim 1, wherein the polymerization is carried out for 15 to 30 seconds.

9. The method according to claim 1, wherein the liquid polymerizable mixture comprises an initiator selected from the group consisting of camphorquinone, ethyl 4-(dimethylamino) benzoate (EDMAB), 2,4,6-trimethylbenzoyldiphenylphosphine oxide, 1-Phenyl-1,2 propanedione, N,N-dimethyl-p-toluidine, benzoyl peroxide, and any combination thereof.

10. The method according to claim 1, wherein the liquid polymerizable mixture comprises an inhibitor selected from the group consisting of hydroquinone, mono methyl ether hydroquinone, 4-methoxyphenol, 4-tert-butylcatechol, and any combination thereof.

11. The method according to claim 1, wherein there are pre-formed reservoirs on the surface(s) of the medical device.

12. The method according to claim 11, wherein the reservoirs are formed on the surface(s) of the medical device before the liquid polymerizable mixture is applied.

13. The method according to claim 1, wherein the macromer comprises a block co-polymer composed of covalently bonded (polylactic acid)2-PEG 200-(polylactic acid)2 and end-capped with at least one of acrylate and methacrylate groups at both ends.

14. The method according to claim 1, wherein the macromer comprises a covalently bonded (polylactic acid)4-PEG 200-(polylactic acid)4 and end-capped with at least one of acrylate and methacrylate groups at both ends.

15. The method according to claim 2, wherein the anesthetic agent is selected from the group consisting of bupivacaine, lidocaine, and ropivacaine.

16. The method according to claim 1, wherein one bioactive agent is an antimicrobial agent selected from the group consisting of penicillin, imipenem, cefotaxime, ceftaroline, kanamycin, gentamycin, tobramycin, carbapenems, teicoplanin, dalbavancin, vancomycin, cefazolin, oritavancin, daptomycin, dalfopristin, amphomycin, colistins, ramoplanin, azithromycin, cethromycin, erythromycin, rifamycin, rifapentin, rifaximin, minocycline, tigecicline, linezolid, clindamycin, ciprofloxacin, rifampin, and any combination thereof.

17. The method according to claim 1, wherein the liquid polymerizable mixture further comprising at least a macromer that is a liquid at a temperature between about 10° C. and about 40° C. without addition of a solvent, and at least one selected from the group consisting of (i) at least one initiator, and (ii) an at least one inhibitor.

18. The method according to claim 2, wherein the liquid polymerizable mixture further comprising at least a macromer that is a liquid at a temperature between about 10° C. and about 40° C. without addition of a solvent, and at least one selected from the group consisting of (i) at least one initiator, and (ii) an at least one inhibitor.

* * * * *